(12) United States Patent
Wheeler et al.

(10) Patent No.: US 9,157,550 B2
(45) Date of Patent: Oct. 13, 2015

(54) MICROFLUIDIC SYSTEMS AND METHODS

(75) Inventors: Matthew B. Wheeler, Tolono, IL (US); Dongshin Kim, Lexington, MA (US); David J. Beebe, Monona, WI (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1058 days.

(21) Appl. No.: 12/652,735

(22) Filed: Jan. 5, 2010

(65) Prior Publication Data

US 2010/0234674 A1     Sep. 16, 2010

Related U.S. Application Data

(60) Provisional application No. 61/142,605, filed on Jan. 5, 2009.

(51) Int. Cl.
*C12M 1/34* (2006.01)
*F16K 99/00* (2006.01)
(Continued)

(52) U.S. Cl.
CPC ......... *F16K 99/0001* (2013.01); *F16K 99/0017* (2013.01); *F16K 99/0028* (2013.01);
(Continued)

(58) Field of Classification Search
CPC ............ F16K 99/0001; F16K 99/0017; F16K 99/0028; A61B 17/425; B01L 3/5085; B01L 2300/0829; C12M 21/06; C12M 23/12; C12M 23/16; C12M 41/46
USPC ...................................................... 435/288.5
See application file for complete search history.

(56) References Cited

U.S. PATENT DOCUMENTS

| 4,676,274 A | 6/1987 | Brown |
| 4,832,759 A | 5/1989 | Curtis et al. |

(Continued)

FOREIGN PATENT DOCUMENTS

| WO | WO 91/15750 | 10/1991 |
| WO | WO 93/22053 | 11/1993 |

(Continued)

OTHER PUBLICATIONS

Diao et al. "A three-channel microfluidic device for generating static linear gradients and its application to the quantitative analysis of bacterial chemotaxis." Lab Chip, vol. 6 (2006), pp. 381-388.*

(Continued)

*Primary Examiner* — William H Beisner
(74) *Attorney, Agent, or Firm* — Greer, Burns & Crain, Ltd.

(57) ABSTRACT

Microfluidic systems and methods. A microfluidic device for in vitro fertilization comprises a substrate and a plurality of microchannels disposed in the substrate, including an inlet of at least two of the plurality of microchannels arranged on the substrate to align with a fluid-handling device. Another microfluidic system for assaying a plurality of cells comprises a substrate and a plurality of microfluidic channels comprising a source channel, a sink channel, and a cell chamber. An insert for a microfluidic system comprises a substrate configured to be inserted into a dish and a plurality of microscale wells disposed in the substrate. A microfluidic channel comprises a substrate and at least one microchannel having an open inlet, an open outlet, a channel, and an opening in the substrate disposed over a portion of the channel. A device for providing an amount of fluid for a fluidic system comprises a main reservoir, an aspiration well, tubing coupling the reservoirs, and a seal closing the main reservoir. Air tubing having a hydrophobic end extends into the at least one aspiration well.

25 Claims, 16 Drawing Sheets

(51) Int. Cl.
 C12M 3/06 (2006.01)
 C12M 3/00 (2006.01)
 A61B 17/425 (2006.01)
 B01L 3/00 (2006.01)

(52) U.S. Cl.
 CPC ............. *A61B17/425* (2013.01); *B01L 3/5085* (2013.01); *B01L 2300/0829* (2013.01); *C12M 21/06* (2013.01); *C12M 23/16* (2013.01); *Y10T 137/0318* (2015.04); *Y10T 137/87249* (2015.04)

(56) References Cited

U.S. PATENT DOCUMENTS

| | | | |
|---|---|---|---|
| 5,296,375 | A | 3/1994 | Kricka et al. |
| 5,304,487 | A | 4/1994 | Wilding et al. |
| 5,376,252 | A | 12/1994 | Ekstrom et al. |
| 5,427,946 | A | 6/1995 | Kricka et al. |
| 5,486,335 | A | 1/1996 | Wilding et al. |
| 5,498,392 | A | 3/1996 | Wilding et al. |
| 5,512,476 | A | 4/1996 | Gordon |
| 5,525,515 | A | 6/1996 | Blattner |
| 5,635,358 | A | 6/1997 | Wilding et al. |
| 5,637,469 | A | 6/1997 | Wilding et al. |
| 5,691,194 | A | 11/1997 | Gordon |
| 5,744,366 | A | 4/1998 | Kricka et al. |
| 5,757,482 | A | 5/1998 | Fuchs et al. |
| 5,779,868 | A | 7/1998 | Parce et al. |
| 5,989,835 | A | 11/1999 | Dunlay et al. |
| 6,193,647 | B1 | 2/2001 | Beebe et al. |
| 6,695,765 | B1 | 2/2004 | Beebe et al. |
| 6,818,403 | B2 * | 11/2004 | Kirk et al. ............... 435/6.14 |
| 7,022,516 | B2 * | 4/2006 | Kanegasaki et al. ....... 435/288.3 |
| 7,947,491 | B2 * | 5/2011 | Jeon et al. ............... 435/288.5 |
| 2007/0275455 | A1 | 11/2007 | Hung et al. |

FOREIGN PATENT DOCUMENTS

| | | |
|---|---|---|
| WO | WO 93/22055 | 11/1993 |
| WO | WO 97/47390 | 12/1997 |
| WO | WO 03/008102 A1 | 1/2003 |
| WO | WO 2004/108011 A1 | 12/2004 |
| WO | WO 2007/08609 A2 | 1/2007 |

OTHER PUBLICATIONS

Shamloo et al. "Endothelial cell polarization and chemotaxis in a microfluidic device." Lab Chip, vol. 8 (2008), pp. 1292-1299.*
S.J. Choi, I. Glasgow, H. Zeringue, D.J. Beebe, M.B. Wheeler, "Development of Microelectromechanical Systems to Analyze Individual Mammalian Embryos; Embryo Biocompatibility," Biol. Reprod., vol. 58 (Suppl. 1), p. 96 (abstr.), 1998.
K. Chun, G. Hashiguchi, H. Toshiyoshi, H. Fujita, "An Array of Hollow Microcapillaries for the Controlled Injection of Genetic Materials into Animal/Plant Cells," presented at Technical Digest of Twelfth IEEE International Conference on Micro Electro Mechanical Systems (MEMS '99), Orlando, FL, 1999, pp. 406-411.
Sherrie G. Clark et al., "Reduction of polyspermic penetration using biomimetic microfluidic technology during in vitro fertilization," The Royal Society of Chemistry 2005, Lab Chip. 2005, 5, 1229-1232.
I.K. Glasgow, H.C. Zeringue, D.J. Beebe, S.J. Choi, J.T. Lyman, M.B. Wheeler, "Individual Embryo Transport and Retention on a Chip for a Total Analysis System," presented at the Solid-State Sensor and Actuator Workshop, Hilton Head Island, SC, 1998.
I.K. Glasgow, H.C. Zeringue, D.J. Beebe, S.J. Choi, J.T. Lyman, M.B. Wheeler, "Individual Embryo Transport and Retention on a Chip," in Micro Total Analysis Systems '98; Proceedings of the TAS '98 Workshop held in Banff, Canada, D.J. Harrison and A. van den Berg, Eds. Boston; Kluwer Academic Publishers, pp. 199-202, 1998.

Debra L. Hickman et al., "Comparison of Static and Dynamic Medium Environments for Culturing of Pre-implantation Mouse Embryos," Comparative Medicine Apr. 2002; 52(2): 122-126.
K. Hosokawa, T. Fujii, I. Endo, "Hydrophobic Microcapillary Vent for Pneumatic Manipulation of Liquid in μTAS," in Micro Total Analysis Systems '98; Proceedings of the TAS '98 Workshop held in Banff, Canada, D.J. Harrison and A. van den Berg, Eds. Boston: Kluwer Academic Publishers, pp. 307-310, 1998.
C.L. Keefer, S.L. Stice, A.M. Paprocki, P. Golueke, "In vitro Culture of Bovine IVM-IVF Embryos: Cooperative Interaction Among Embryos and the Role of Growth Factors," Theriogenology, vol. 41, pp. 1323-1331, 1994.
M. Lane and D.K. Gardner, "Selection of Viable Mouse Blastocysts Prior to Transfer using a Metabolic Criterion," Human Reproduction, vol. 21. No. 9, 1996, pp. 1975-1978.
P.C.H. Li and D.J. Harrison, "Transport, Manipulation, and Reaction of Biological Cells on—Chip Using Electrokinetic Effects," Analytical Chemistry, vol. 69, No. 8, pp. 1564-1568, 1997.
J.M. Lim, B.C. Reggio, R.A. Godke, W. Hansel, "A Continuous Flow, Perifusion Culture System for 8- to 16-Cell Bovine Embryos Derived from In Vitro Culture," Theriogenology, vol. 46, pp. 1441-1450, 1996.
M.d.C. Lopez-Garcia et al., "Sperm motion in a microfluidic fertilization device," Biomed Microdevices (2008) 10:709-718.
Melin, J., W. van der Winjingaart, and G. Stemme, "Behaviour and design considerations for continuous flow closed-open-closed liquid microchannels," Lab on a Chip, 2005, 5(6): p. 682-686.
Meyvantsson et al., "High Throughput Microfluidies," In Annual Fall Meeting of Biomedical Engineering Society, 2006, Chicago, IL, USA.
J.A. Pruitt, D.W. Forrest, R.C. Burghardt, J.W. Evans, D.C. Kraemer, "Viability and Ultrastructure of Equine Embryos Following Culture in a Static or Dynamic System," Journal of Reproduction and Fertility, vol. 44 (Supp.), pp. 405-410, 1991.
Stephanie Raty et al., "Embryonic development in the mouse is enhanced via microchannel culture," Miniaturisation for Chemistry, Biology & Bioengineering, Lab Chip. 2004, 4,186-190.
G.D. Smith et al., "Gamete and embryo isolation and culture with microfluidics," Theriogenology 68S (2007) S190-195.
Ronald S. Suh et al., "IVF within microfluidic channels requires lower total numbers and lower concentrations of sperm," Human Reproduction, vol. 21, No. 2, pp. 477-483, 2006.
Ronald S. Suh et al., "Rethinking gamete/embryo isolation and culture with microfluidics," Human Reproduction Update, vol. 9, No. 5, pp. 451-461, 2003.
Vajta et al., "New Method for Culture of Zona-Included or Zona-Free Embryos: The Well of the Well (WOW) System," Molecular Reproduction and Development 55:256-264 (2000).
Walker et al., "A passive pumping method for microfluidic devices," Lab On a Chip, 2002, 2(3): p. 131-134.
Eric M. Walters et al., "Mammalian Embryo Culture in a Microfluidic Device," Methods in Molecular Biology, vol. 254, 375-382.
M.B. Wheeler, S.J. Choi, I.K. Glasgow, H.C. Zeringue, J.T. Lyman, D.J. Beebe, "Development of Microelectromechanical Systems to Analyze Individual Mammalian Embryos: Embryo Biocompatability and Individual Embryo Transport on Silicon a Chip," Arquivos da Faculdade de Veterinaria UFRGS, Sociedade Brasileira de Transferencia de Embraoes, vol. 26, No. 1, 1998 (Supl), p. 391.
M.B. Wheeler et al., "Developments in in vitro technologies for swine embryo production," Reproduction, Fertility and Development 2004, 16, 15-25.
Matthew B. Wheeler et al., "Application of sexed semen technology to in vitro embryo production in cattle," Theriogenology 65 (2006) 219-227.
M.B. Wheeler et al., "Toward culture of single gametes: The development of microfluidic platforms for assisted reproduction," Theriogenology 68S (2007) S178-S189.
"Microchip Arrays put DNA on the Spot," Science Magazine, vol. 282, Oct. 16, 1998, pp. 396-405.

* cited by examiner

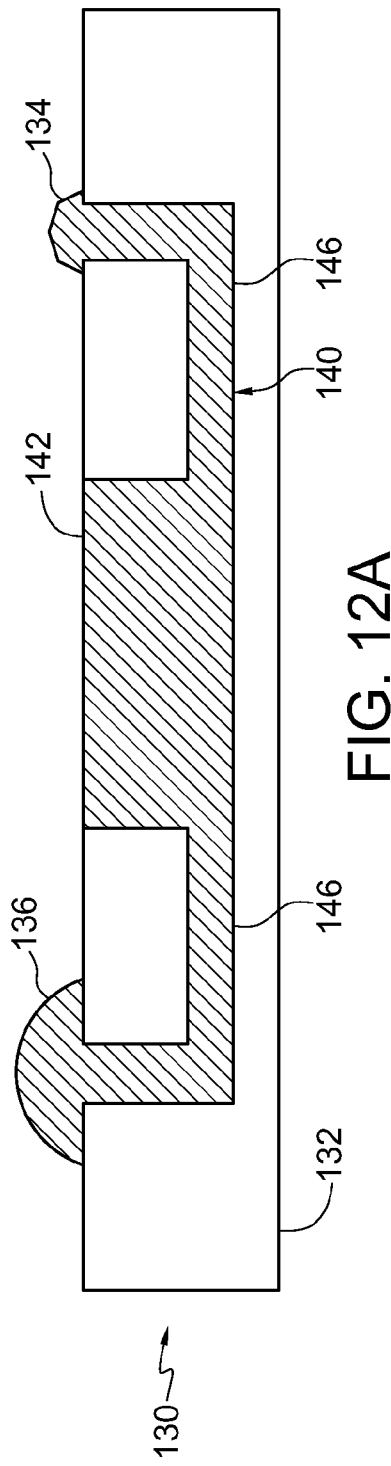
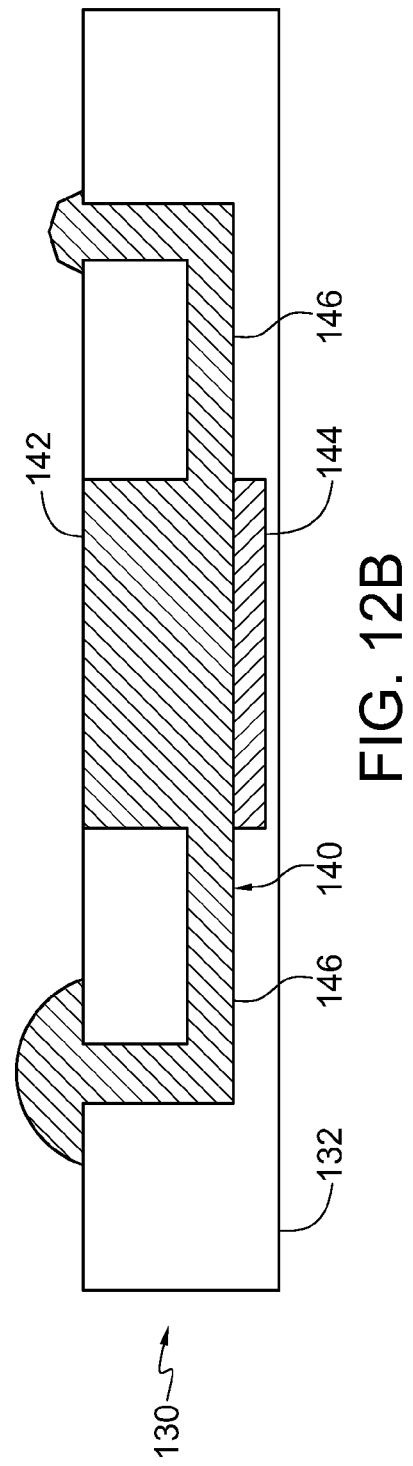

MICROFLUIDIC SYSTEMS AND METHODS

PRIORITY CLAIM AND REFERENCE TO RELATED APPLICATION

This application claims the benefit of U.S. Provisional Application Ser. No. 61/142,605, filed Jan. 5, 2009, under 35 U.S.C. §119.

STATEMENT OF GOVERNMENT INTEREST

This invention was made with Government assistance under Grant No. 1-600207-538026-538393 issued by U.S. Department of Agriculture (USDA). The Government has certain rights in the invention.

FIELD OF THE INVENTION

A field of the invention is microfluidics. Example applications of the invention include methods and systems for microfluidic handling of cells.

BACKGROUND OF THE INVENTION

Microfluidic systems and methods are becoming increasingly significant for providing benefits of much larger systems or facilities (such as, but not limited to, laboratories or biological environments) with increased efficiency as well as reduced size, cost, and/or complexity. Such microfluidic systems and methods have various benefits and advantages for a multitude of applications, including but not limited to the area of biology.

As one nonlimiting example, technology assisted reproduction techniques in which embryos are handled independently from their mammalian biological source are growing in importance and frequency of use. For example, such techniques have great direct benefit to persons unable to have babies through unassisted sexual reproduction. The agricultural industries also increasingly rely upon such assisted reproduction techniques. Embryo manipulation is used in livestock reproduction to control such things as the faster genetic evolution of cattle and permitting the genetic characteristics of a single exceptional cow or bull to be passed on to far greater numbers of offspring than would be possible through unassisted sexual reproduction.

In-vitro fertilization (IVF) is an appropriate microfluidic application, since microfluidic technology can provide accurate control of a micro-environment surrounding the cells. An example of microfluidic technology for IVF is described in U.S. Pat. No. 6,695,765 (the '765 patent), which is incorporated in its entirety by reference herein.

Livestock embryo manipulation is becoming more routine due to the development of gene manipulation, cloning, and IVF techniques. The overall goal of embryo manipulation in livestock is to increase production efficiency, especially with regard to reproduction, milk production, or production of specific milk components, lean tissue growth with reduced fat content, and/or decreased susceptibility to specific diseases. Embryo transfer is also used to introduce or rescue valuable germplasm and propagate rare breeding animals such as endangered exotic species.

Expense and relatively low success rates place significant burdens on the use of these assisted reproduction techniques for humans as well as livestock. In human reproduction such expense and failure adds emotional as well as economic burdens. In addition, safeguards against failures often result in multiple births, as well as additional stored embryos. Expense is the primary concern in livestock reproduction. Failure rates in reproduction techniques as well as testing and other embryo handling techniques are attributable primarily to the significant handling and manipulation of embryos in executing these techniques.

Microfluidic systems can be applied to other types of biological systems. Another example application for a microfluidic system is to create an in-vivo-like culture microenvironment for embryos. Yet another example application is a microchannel system including passive pumping, for cell/embryo/oocyte culture and chemical analysis. Still another example microfluidic system is used for cell testing.

SUMMARY OF THE INVENTION

According to embodiments of the present invention, a microfluidic device for in vitro fertilization is provided. The microfluidic device comprises a substrate, and a plurality of microchannels disposed in the substrate, wherein each of the microchannels includes an inlet at an end for receiving a cell and an outlet at an opposing end. Each of the microchannels further comprises a restriction disposed near the outlet. An inlet of at least two of the plurality of microchannels is arranged on the substrate to align with a fluid-handling device.

According to another embodiment of the invention, a microfluidic system is provided for assaying a plurality of cells. The microfluidic system comprises a substrate and a plurality of microfluidic channels arranged in the substrate. Each of the plurality of microfluidic channels comprises a source channel at an end of the microfluidic channel and a sink channel at an opposing end, the source channel having an inlet and an outlet. A cell chamber is disposed within the microfluidic channel between the source channel and the sink channel, and a cell inlet is provided in fluid communication with the cell chamber. A fluidic resistance is disposed between the cell chamber and one of the sink channel and the source channel.

According to another embodiment of the invention, an insert for a microfluidic system is provided. The insert comprises a substrate and a plurality of microscale wells disposed in the substrate. Each of the plurality of microscale wells has a predetermined size, and the plurality of microscale wells are uniformly distributed in the substrate. Each of the plurality of microscale wells is fabricated in the substrate using soft lithography. The substrate is configured to be inserted into a dish.

According to yet another embodiment of the present invention, a microfluidic channel is provided. The microfluidic channel comprises a substrate and at least one microchannel disposed in the substrate. Each of the at least one microchannel comprises an open inlet at one end, an open outlet at an opposing end, a channel within the substrate and disposed between the inlet and the outlet, and an opening in the substrate disposed over a portion of the channel to expose an open portion of the channel.

According to another embodiment of the present invention, a device is provided for providing an amount of fluid for a fluidic system. The device comprises a first reservoir providing a main reservoir, at least one second reservoir separate from the first reservoir and providing an aspiration well, a siphon tubing coupling the first reservoir and the at least one second reservoir, and a seal closing the first reservoir. An air tubing extends through a portion of the seal, and the air tubing is coupled to the at least one second reservoir and has an end extending into the at least one second reservoir. The end of the air tubing is hydrophobic.

Example embodiments are described herein. However, it will be appreciated that embodiments of the present invention disclosed herein can be used alone or in any combination to provide any of various microfluidic systems and methods.

BRIEF DESCRIPTION OF THE DRAWINGS

FIGS. 6A-6B show a microfluidic well insert for a well of the well (WOW) system according to an embodiment of the present invention, wherein FIG. 6B shows wells and channels for the insert of FIG. 6A;

FIGS. 12A-12B show a microfluidic channel including an open-closed-open-closed-open (OCOCO) system according to another embodiment of the present invention:

DETAILED DESCRIPTION

Figure 1:
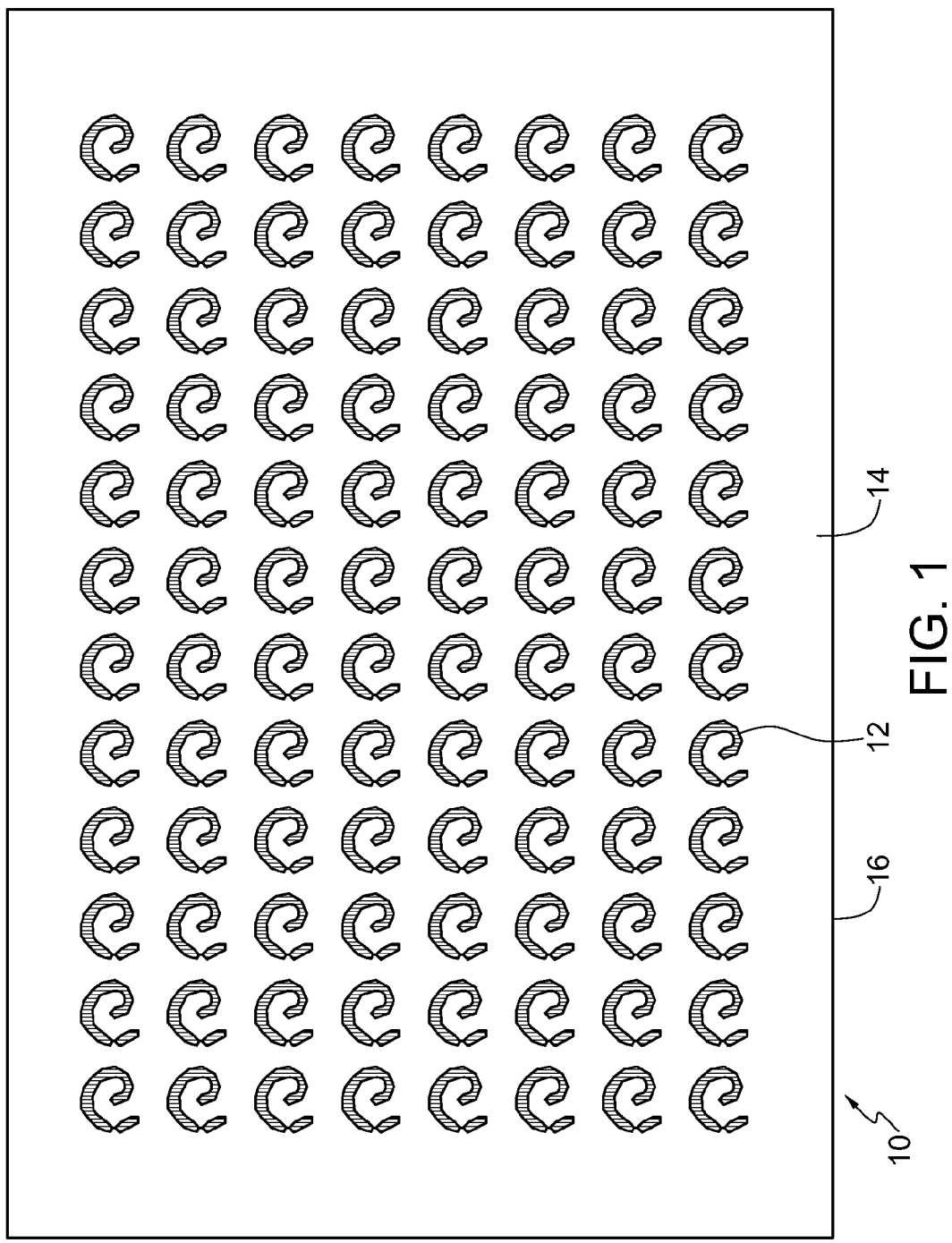
FIG. 1 shows a microfluidic device for IVF, according to an embodiment of the present invention.

The present inventors have discovered that IVF systems conventionally provide a low yield, due to inefficiencies in the system, damage to cells contained within the system, difficulty in accessing cells, and other reasons, and thus require an undesirable cost. Embodiments of the present invention provide, among other things, microfluidic systems and methods that improve yield over conventional systems and methods. Such systems can be used alone or in any combination and/or number to provide various benefits and advantages. For example, by providing a plurality of arrayed devices, throughput can be significantly increased for applications such as, but not limited to, IVF and chemotaxis. Additionally, by sizing wells of a particular microfluidic system according to certain species and fabricating an insert to include such sized wells, with or without fluidic channels connecting the wells, a flexible platform is provided for accommodating a wide variety of animal species. According to other embodiments of the present invention, an open-closed-open-closed-open (OCOCO) system is provided for efficient cell culture and convenient sample access. In other embodiments of the present invention, an automatic top-off system is provided using a surface tension valve, which requires neither moving parts nor electronic control devices. One or more of these various embodiments may be combined to provide microfluidic systems, such as but not limited to systems for cell-based microfluidic manipulation (e.g., a high-throughput IVF device), cell-based assay devices (e.g., stem-cell-based assay devices), or other systems or devices. "Microfluidic" as used herein is intended to generally refer to a scale on the order of, but not limited to, 20-1000 microns along at least one dimension for channels.

Many of the devices and systems according to embodiments of the present invention can be provided by microfabrication techniques. In particular, nonlimiting examples, microchannels, inlet and outlet ports, constrictions, fluid resistance, openings, and other components can be microfabricated in a substrate of a suitable material, which can then provide, alone or in combination with other products or apparatus (such as, but not limited to, surfaces of dishes or other bases or substrates), features of embodiments of the present invention. As one nonlimiting example, walls of microchannels can be formed in a microfabricated substrate, and the substrate can be placed on or over and coupled with (e.g., adhered, mounted, resting on, etc.) a flat surface of a base or substrate of glass, silicon, plastic, and other materials to complete the microchannel. In other embodiments, multiple layers formed by microfabricated substrates can be used to provide substrates having particular features. In still other embodiments, injection molding may be used to provide substrates having one or more features. Such microfabricated substrates themselves are considered to be part of the present invention. These substrates can be customized for particular uses, packaged individually or as sets or kits, and/or combined in any way needed. Such techniques can be used alone or in combination to provide particular embodiments of the present invention.

Preferred embodiments will now be discussed with respect to the drawings. The drawings include schematic figures that are not to scale, which will be fully understood by skilled artisans with reference to the accompanying description. Features may be exaggerated for purposes of illustration. From the preferred embodiments, artisans will recognize additional features and broader aspects of the invention.

High-Throughput In-Vitro Fertilization (IVF) Device

For many species, under optimal conditions, conventional methods of IVF may be sufficient, particularly when plenty of semen is available (e.g., human, cattle). However, for fertilization with limited or special (e.g., selective, sorted) semen (e.g., a pig), or where there is a low fertilization amount, an insufficient amount of semen may be available, resulting in a lower and/or unacceptable yield under conventional IVF methods. It is desired to provide a low handling, high throughput IVF device and method to provide a higher yield while requiring significantly less sperm than conventional methods.

Example embodiments of the present invention provide a high throughput, automated IVF device, which can require much less sperm than conventional methods and devices. Example embodiments allow sorting of sperm directly into a smaller volume for IVF. In this way, smaller amounts or numbers of sperm (as a nonlimiting example, 20-100) are needed.

In an example embodiment, at least one microchannel is provided in which a biologically compatible fluid is provided. Examples include but are not limited to SOF, PALP, modified Whitten's medium, $CRI_{aa}$, Ham's F-10, TCM-199, DMEM, M2, M16, G1, G2, and others. The at least one microchannel is used to incubate cells, such as but not limited to oocytes and embryos (human and animal), or any other type of adherent or non-adherent cells. In a nonlimiting example, one or more of the microchannels is aligned to match manual or automated systems, such as but not limited to a handheld pipettor, a single-head or multi-head pipettor of a fluid handling robot, and/or a dispenser of a flow cytometer.

FIG. 1 shows a nonlimiting example high-throughput IVF device 10 according to the present invention, including an array of microchannels 12 for incubating oocytes and embryos. In the example IVF device 10 shown in the figures below, 96 microchannels are provided, allowing handling of 96 oocytes simultaneously. This number can be lower or higher (e.g., 192 or more microchannels). In the example shown below, a two-dimensional array of microchannels (8×12) is provided, though other arrangements are possible. The microchannels in FIG. 1 are formed within a substrate 14, for example a mold from PDMS, polystyrene, injection-molded plastic, etc., and the substrate can be disposed on a base 16 or substrate of a suitable material, such as but not limited to polystyrene, COC, glass, silicon wafer, or any biocompatible plastic material. In a nonlimiting example embodiment, the microchannels 12 formed within the substrate material and the surface of the base can combine to provide the microchannels. Other possible example materials for the high-throughput IVF device 10 are provided in the '765 patent. The example device 10 may be formed by, for instance, microfabrication techniques, injection molding, etc.

FIGS. 2A-2F show an example of an individual microchannel 12 at six stages of an example IVF method. Preferably, each microchannel 12 is sized in suitable proportion to an embryo and configured to approximate a path sperm would take for fertilization. Nonlimiting examples of suitable proportions for the microchannel 12 approximate a size of an embryo or oocyte, and as a nonlimiting example are up to 250 microns high by 1000 microns wide. Nonlimiting example configurations include spiral, straight, arced, etc., depending on need, configuration of a fluid handler, etc. The microchannels 12 for these and other embodiments may be square in cross-section, for instance, or have other cross-sectional shapes. In a nonlimiting example, each microchannel 12 is generally spiral-shaped, having (in this example) a centrally (of the spiral) accessible inlet 20 at one end of the microchannel. An outlet well 22 is disposed at an opposed end of the microchannel. Fluid flow through the microchannels 12 takes place via capillary action or passive pumping. The inlet 20 and the outlet 22 may be accessible, for example, by manual or automatic tools such as but not limited to a fluid handling robot, a flow cytometer (e.g., multi-head flow cytometer), a hand pipette (e.g., a multi-head pipettor), etc. In an example embodiment, the microchannels 12 are configured and arranged so that the array of inlets 20 and the outlets 22 are accessible (e.g., aligned to match with) a multi-head device such as a multi-head pipettor of a fluid handling robot, a dispenser, a pipette, a flow cytometer, etc. This example microchannel configuration and inlet alignment allows a fluid handling robot, for example, to sort fewer numbers of sperm than needed for similar results in conventional IVF methods. The microchannels 12 may be of equal or differing size and/or configuration. As an amount of fluid is added to the microchannel 12, an approximately equal amount can be removed from the outlet 22 for managing the size of droplets and maintaining the flow characteristics.

A constriction 24 is provided within the (generally spiral, in this example) microchannel 12. As shown in FIG. 2A-2D, the constricted area (e.g., funnel-shaped or other shapes or configurations, such as those disclosed in the '765 patent) is provided for the oocyte so that the oocyte will become concentrated, similar to a fallopian tube in a mammal. The constriction 24 should allow fluid flow but prevent the oocyte/embryo from passing the constriction (e.g., 10-50 microns).

Figure 2C:
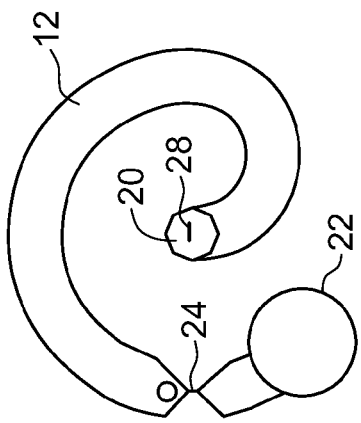
FIGS. 2A-2F show stages in an example IVF method using the device of FIG. 1.
Figure 2F:
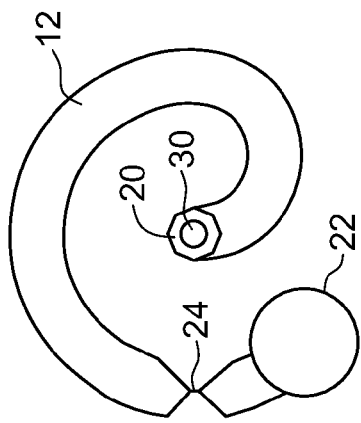
Figure 2B:
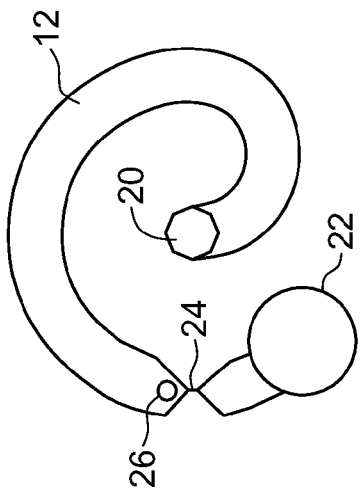
Figure 2E:
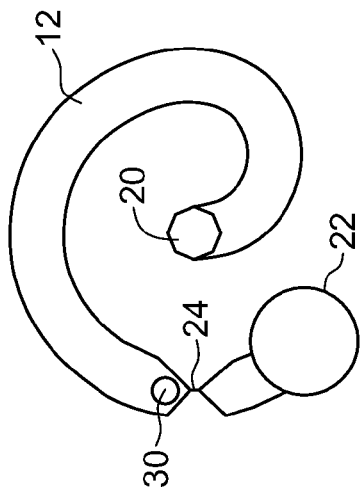
Figure 2A:
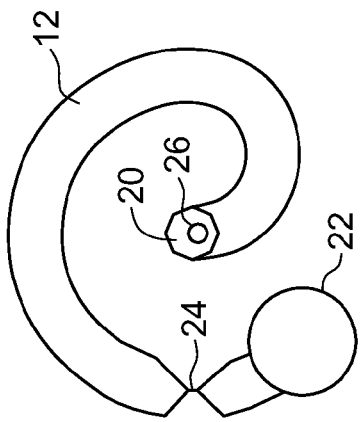
Figure 2D:
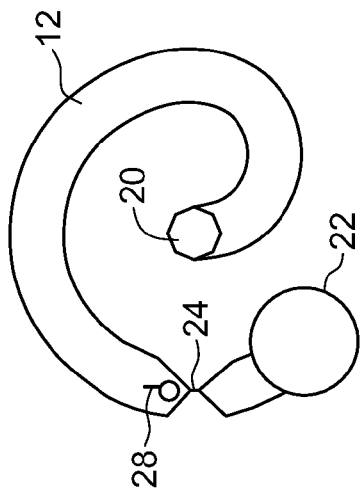

In an example IVF method using the example device, oocytes 26 are introduced into the at least one microchannel 12 (FIG. 2A) using a method such as but not limited to introducing an oocyte in the microchannel via the inlet 20 from a multi-head pipettor of a fluid handling robot or via manual means. The oocyte 26 becomes parked at or near the constriction 24 (FIG. 2B). After a particular amount of incubation time, determined based on any suitable measure (e.g., depending on species), sorted or non-sorted sperms 28 are introduced into the at least one microchannel inlet 20 (FIG. 2C) using automated or manual methods such as a multi-head flow cytometer or by other ways (e.g., hand pipetting). The sperm 28 swims or is moved by flow to the oocyte 26 (FIG. 2D), and the oocyte is fertilized (FIG. 2E). The example microchannel shape shown in FIGS. 1-2F and flow control allow the sperm 28 to be directed to the oocyte 26 target. By contrast, in some conventional IVF methods, an oocyte is provided in a droplet on a Petri dish, and the sperm then are intended to randomly go to the target.

Once fertilized, the embryos 30 are moved to the inlet 20 (FIG. 2F), such as by generating a reverse flow (e.g., as disclosed in the '765 patent), or by other methods (e.g., negative pressure, such as by using a pipette) and collected at the inlet, for example by manual methods or by using automated methods such as the fluid handling robot. The embryos 30 may be removed by interfacing with the inlet 20, e.g., by using the fluid handling robot, and are ready for further steps as necessary.

Systems 10 and methods of the present invention provide significant advantages over known IVF systems and methods. By expanding the yield versus conventional IVF methods by the number of arranged microchannels or a portion thereof (as a nonlimiting example, 96 times or beyond), systems and methods of the present invention address the low yield of conventional IVF methods.

Further, because at least one microchannel 12 is used, a microenvironment can be controlled precisely without inducing shear stress on cells. Higher yield is provided by, among other things, the high-throughput manner provided by the multiple microchannels in example embodiments.

High-Throughput Migration Device to Study Chemotaxis

Chemotaxis is a phenomena of cell motility, which is related to cell viability, cancer development, and wound healing. For example, many disease states involve the migration of certain cells (such as, but not limited to, immune cells, bone marrow cells, stem cells, etc.) to a particular area, e.g., an area of infection, injury, cancer, etc. If the cells move in response to a certain agent, this is a sign of viability. Chemotaxis devices thus provide an assay whereby the devices assess the viability of certain cells to move toward a particular area. In an example method, injury is induced, and stem cells are injected. It is determined whether the cells target the injury or defect by migrating to the area of injury or defect. In another example method, cancer cells are known to send out signals to certain cells.

Many chemotaxis devices have been developed that are not suitable to perform high-throughput chemotaxis studies. For example, conventional chemotaxis methods using such devices are laborious and time consuming, at least because the time waiting for cell migration can be lengthy. Such methods also may not be very accurate. Further, large amounts of expensive growth factors are required.

Embodiments of the present invention provide, among other things, the use of fluidic resistance to prevent convection and provide a flow barrier. In this way, example embodiments can create cell chambers that can create a defined concentration gradient. Interruption of the concentration gradient is minimized due to the fluidic resistance, and thus cell to cell factors are conserved inside the cell chamber.

Figure 3:
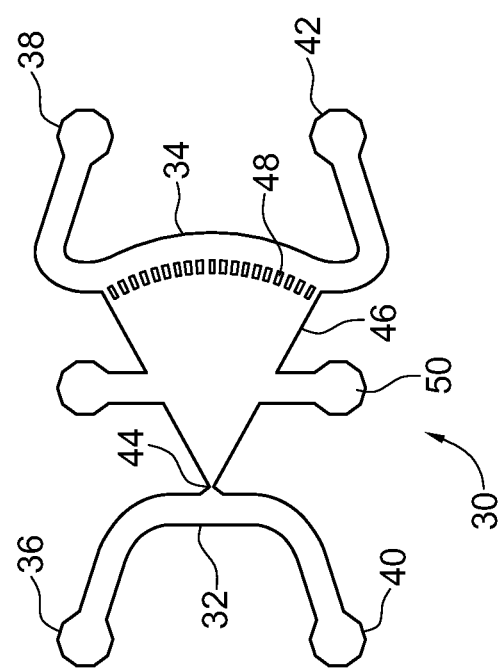
FIG. 3 shows an example microfluidic migration device according to another embodiment of the present invention.

FIG. 3 shows an example microfluidic chemotaxis migration device 30. The device 30 includes a source channel 32 and an opposed sink channel 34, each having an inlet 36, 38 and outlet 40, 42 port. Flow occurs within the source channel 32 and the sink channel 34, and, in an example embodiment, diffusion occurs from the source channel (concentration goes from high to low as it diffuses), through a narrow (e.g., wedge) channel 44, and into a cell chamber 46 disposed between the source channel and the sink channel. A fluidic resistance 48, which in the example device 30 is disposed between the cell chamber 46 and the sink channel 34, slows fluid flow. Cell chambers 46 can be rectangular, hourglass, pyramid, or other shapes, and the concentration gradient can change accordingly. The cell chamber shape can be varied according to the experimental purpose, for example. A square shape may be desirable for a simple gradient experiment, whereas a pie shape may be preferred for observing cell-cell interaction on a local cell population (as the local cell population will be going high or low as they migrate toward the center or the circumference, respectively). It is also contemplated that the relative positions of the sink channel 34 and the source channel 32 can be reversed, depending on the concentration gradient desired. Thus, the narrow channel 44 at the center side can be either from the source or the sink channel.

The cell chamber 46 is disposed between the source channel 32 and the sink channel 34, and has at least one cell inlet 50 leading thereto. The fluidic resistance (e.g., protrusions formed within a substrate, array of narrow channels in the substrate, etc.) in this example embodiment separates the cell chamber 46 fluidically from the sink channel 34 but permits passage of molecules by diffusion. The sink channel 34 provides a zero boundary condition to form the concentration gradient within the cell chamber 46. Particular fluidic resistance that is provided can vary depending on the design and experimental conditions. Preferably, the fluidic resistance should be as high as possible to minimize fluid flow through the cell chamber 46, to prevent interrupting the gradient while transport of molecules is allowed by diffusion.

It will be appreciated that the configurations shown and described herein are merely examples, and that other configurations are possible. Example materials for the device 30, fabrication methods, etc. can be similar to those provided for the IVF microchannel 10 described herein, and/or those provided in the '765 patent herein, and techniques for forming the particular features will be appreciated by those of ordinary skill in the art.

Figure 4:
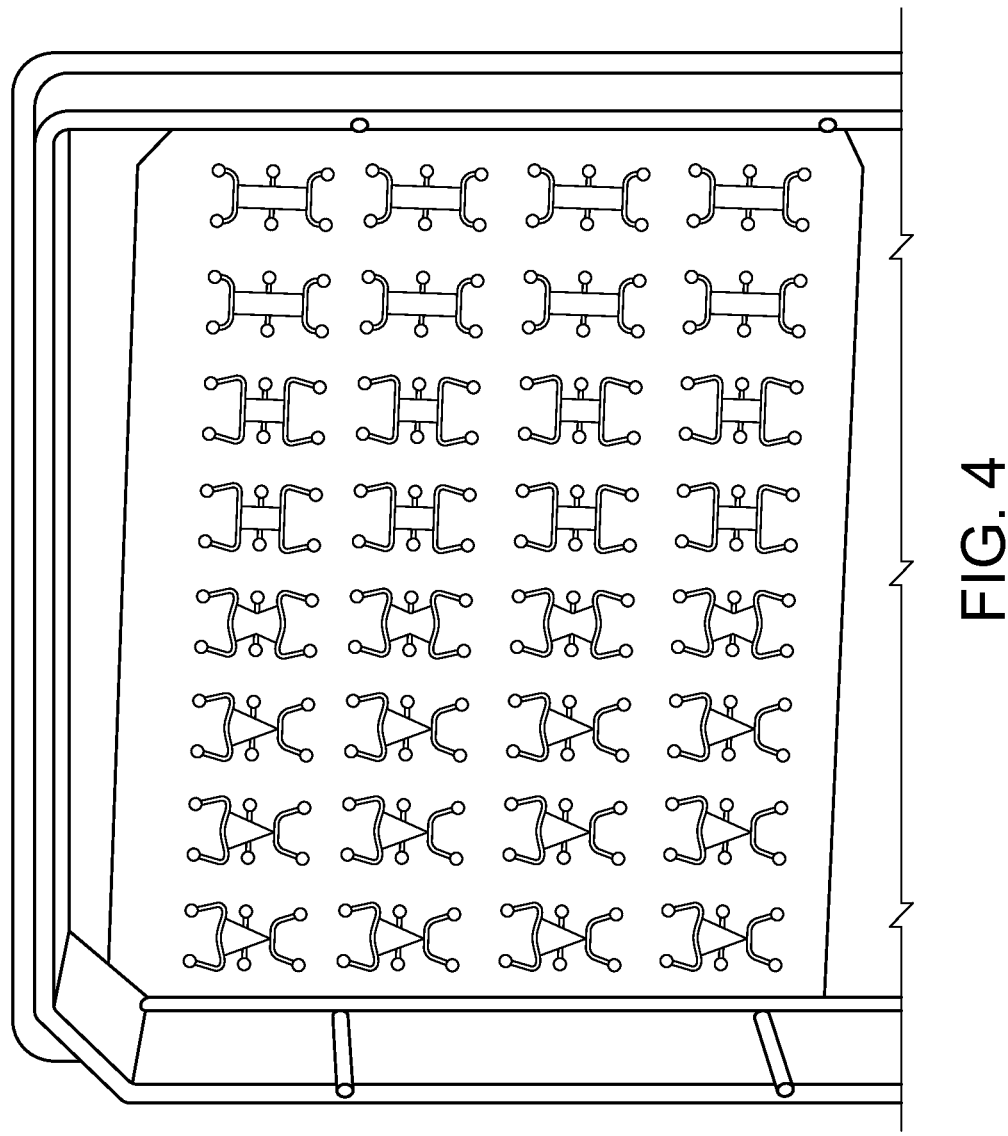
FIG. 4 shows a high-throughput microfluidic system including a plurality of microfluidic migration devices.

A plurality of chemotaxis migration devices 50 may be arranged in a one- or two-dimensional array to provide a high-throughput chemotaxis system, an example of which is shown in FIG. 4. The cell inlet 50, source channel inlet 36 and outlet 40, and sink channel inlet 38 and outlet 42 may be aligned with suitable devices, such as but not limited to those described herein for the IVF device 10, for providing cells, a chemoattractant, and a blank medium, respectively. The number of cell chambers can be expanded to have, as nonlimiting examples, 96, 192, or more individual chambers to perform the chemotaxis in a high throughput way, and thus significantly expanding the yield.

Figure 5:
FIG. 5 shows an example operation of the migration device of FIG. 3, showing a concentration gradient in a cell chamber.

In an example chemotaxis method, as shown in FIG. 5, cells are loaded in the cell chamber 46 through the cell inlet 50, a chemoattractant is introduced into the source channel 32, and blank medium is introduced in the sink channel 34. In a more particular example, the source channel 32, the cell chamber 46, and the sink channel 38 are loaded with medium (making the device 30 fluidically constant) at a suitable speed, cells are loaded into the cell chamber with more medium, and then the source channel is filled with a suitable substance. A gradient develops, an example of which is shown in FIG. 5, and the introduced cells migrate down toward or away from the pyramid or sink depending on the cell's relation to the source material. This process in example embodiments may be observed. Due to the fluidic resistance 48, there is no flow or convection in the cell chamber 46. Accordingly, the concentration gradient is established mainly by diffusion. As shown in the example chemotaxis device in FIG. 5, the gradient can be, but need not be, developed in cylindrical coordinates. FIG. 5 shows a concentration gradient of fluoroscein isothiocyanate (FITC) in a blank medium.

Example embodiments of the present invention provide significant improvements and advantages over conventional chemotaxis systems and methods. Because example systems and methods use diffusion, cell to cell factors are conserved, and the concentration gradient is conveniently controlled. The high-throughput manner of example embodiments of the present invention solves the low yield problem of current chemotaxis methods, significantly expanding the yield—e.g., 96 times or beyond.

Due to the high throughput allowed by providing a plurality of independent chambers in example embodiments, it is possible to consider a large number of factors, e.g., growth factors for genetic analysis. It is also possible to quantify the migration of cells under certain predetermined factors, which can be provided by configuring the individual chambers. Such independent chambers also provide the potential for personalized medicine, where optimal results may be harvested based on results of assaying.

Additionally, the small size of example chambers allows less reagent to be used. The size of such chambers may also allow the physics of particular chambers to be optimized. Individual configurations may be used within an array, and the present invention is not to be limited to arrays of like configurations, or any specific size, number, or configuration of individual chambers.

Microfluidic Well Insert (MWI) for Oocyte/Embryo Culture

Another example embryo technology is nuclear transfer. This technology typically requires a significant amount of time, labor, equipment, etc. to perform, as opposed to other techniques. A microenvironment may be used to help fertilization as well as hold cells together so that they can develop junctions, associations, etc. This is especially helpful for culturing zona pellucida-free oocytes and embryos, where without the zona pellucida, clusters would not otherwise be obtained.

A technique used to hold cells together involves the use of wells, such as in a plastic culture dish. An example of this technique is the so-called well of the well (WOW) system, such as that disclosed in Vajta et al., New Method for culture of zona-included or zona-free embryos: the Well of the Well system; Mol Reprod Dev. 2000 March; 55(3); 256-64. To provide this example WOW system, hot steel rods are manually pressed on a bottom of a plastic culture dish under a stereo-microscope to create one or more small (e.g., microscale) wells for culturing the oocytes/embryos. However, the effectiveness of this technique may depend largely on the configuration of the microwells, and more particularly the ability to manufacture such wells to exacting standards efficiently and consistently. Forming the wells can be tedious, and the resulting wells will likely not be uniform in size, diameter, depth, and distance because they are formed manually. Thus, it is difficult to achieve controlled results.

To facilitate an in-vivo-like culture microenvironment for embryos, embodiments of the present invention provide, among other things, a ready-to-use culture system that can be made using soft lithography, injection molding, or other methods. In an example embodiment, soft lithography or injection molding is used to make an insert that includes wells that are appropriate for particular applications (e.g., microenvironments for particular species). The insert can be placed in or on a base, such as but not limited to placement inside a dish, for performing WOW methods in the base. Using soft lithography techniques, these wells can be tailored to the size of the embryo that is desired to be cultured. Cells in this way can make associations, and then liberate themselves. Also, after suitable sizes are determined, injection molding can be alternatively or additionally used to produce the wells.

Both channel-less and channeled systems are provided according to embodiments of the present invention. An example channel-less system includes a substrate including one or more wells formed in the substrate. The wells preferably are sized based on a characteristic size of the particular species of oocyte/embryo (or other cells) being cultured. This example channel-less system provides a flexible platform that can accommodate a wide variety of animal species.

An example channeled system includes a substrate having formed therein a plurality of microchannels networked between wells, such as but not limited to similar wells as those provided by channel-less embodiments. In this way, channeled embodiments of the present invention allow cell-cell communication to be maintained between oocytes/embryos during medium change. This latter type of system is useful for at least the reason that embryo growth is improved when the embryos are able to communicate with one another, which is true across generally all species. The example channeled system allows the cells to communicate with one another, and further allows embryos to be cultured both individually and in a group. As a nonlimiting example, cells may be disposed side-by-side, but at a distance that is tailored to optimize embryo culture. Variations include, but are not limited to, varying the distance between the wells, spacing, height, dimensions, etc. of the channel to allow or optimize fluid flow, varying the media, etc. Example embodiments of the present invention are particularly useful for culturing zona pellucida-free oocytes and embryos, as the well holds the cells together much as the zona pellicuida would with intact oocytes or embryos. Materials and fabrication methods for the example insert can be similar to those for the IVF and chemotaxis devices.

Example embodiments of the present invention provide, among other things, uniformly distributed wells with specific, predefined dimensions in size, depth, and distance. Note that though the distribution of wells having a particular predetermined configuration is preferably uniform, it is also possible to provide a plurality of different wells, each having specific, predefined dimensions. Even these wells, however, can be particularly defined using fabrication techniques. Thus, culture experiments based on systems and methods of the present invention can generate controlled data. In addition, embodiments of the present invention provide microchannel networks between wells to maintain cell-cell communication during medium change, which is not possible with conventional methods. Because devices according to example embodiments can be provided as inserts, it is very convenient to prepare an embryo culture system. For example, preparing such a system may be performed merely by, for example, attaching the example insert on the bottom of a cell culture dish.

Example embodiments of the present invention are also scalable, since the insert can be placed in any cell culture dish (e.g., 4 wells, 24 wells, a single big dish, etc.), and as many may be provided as needed. Example embodiments can also be incorporated with a robot or automatic fluid handling system to facilitate high-throughput and automatic culture. Devices and systems of the present invention can be expanded into other forms of devices made of different materials, such as but not limited to polystyrene wells with or without channels fixed on a culture dish.

Figure 6A:
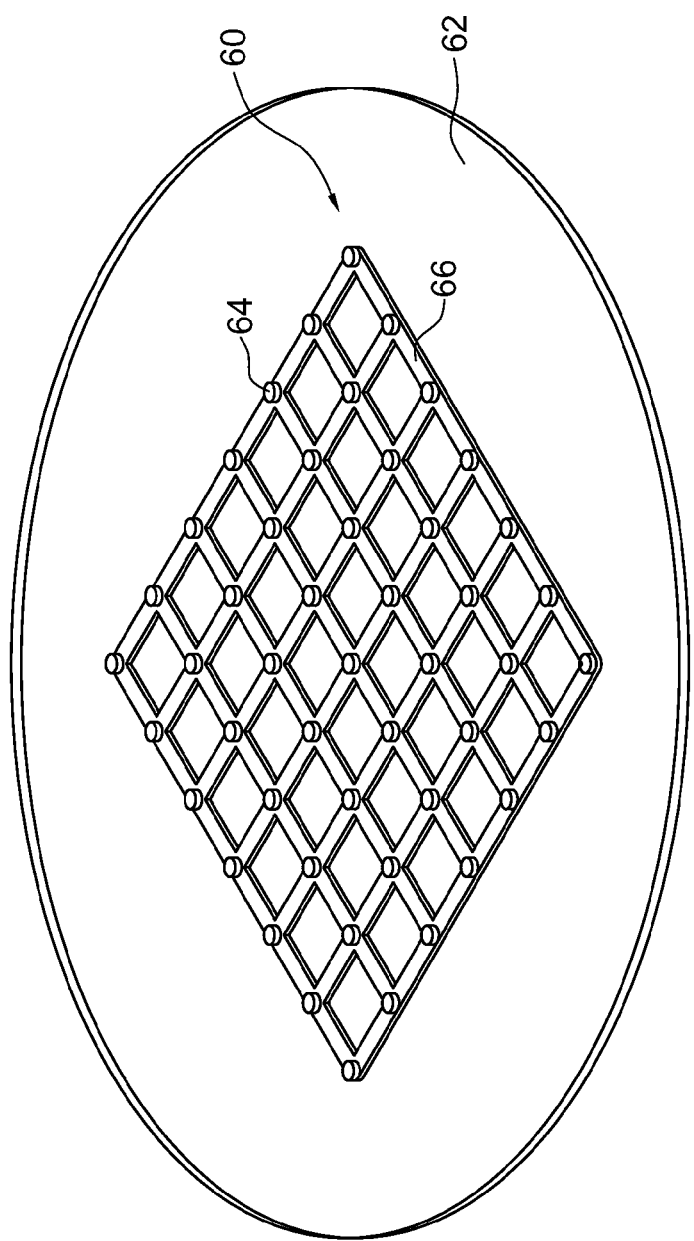
Figure 6B:
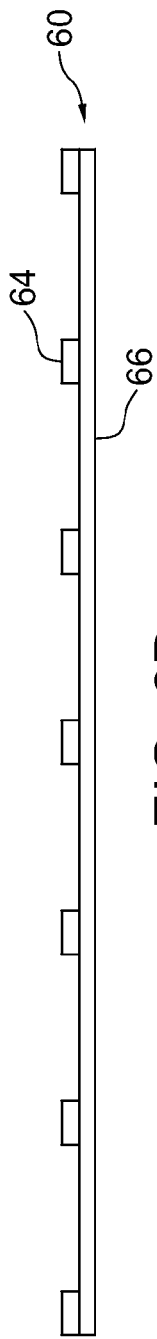

FIG. 6A shows an example channeled microwell insert 60 according to an embodiment of the invention, and FIG. 6B shows an example channel cross-section of the insert. The insert 60 includes a substrate 62 having formed therein a plurality of arrayed microscale wells 64. An example substrate 62 can be sized, shaped, or otherwise modified to be placed in any kind of cell culture dish. A nonlimiting example placement for the design shown in FIG. 6A is for placing in wells of the Nunc four-well culture dish. In the channeled design shown in FIGS. 6A-6B, microscale channels 66 are also formed within the insert 60, disposed between the bottoms of the wells 64 and connecting the wells to one another fluidically. In a channel-less version, by contrast, the wells 64 may be formed within the substrate 62 without providing the connecting channels. In an example embodiment, the insert 60 is formed by pouring PDMS or other material (such as those described herein or in the '765 patent) over a mold similar to the mold shown in FIG. 6B, peeling off after polymerization. This provides the insert, which when placed onto a surface (e.g., of a dish) provides the microchannels. However, it is also contemplated that the microchannels can be formed entirely within PDMS or other fabricated material, and/or formed by joining more than one substrate.

Because the substrate 60 can be configured (e.g., fabricated) to fit any sized dish, example embodiments can be sized to fit conventional or other dishes, while providing consistently-sized microscale wells for the environment within the dish. By simply placing the insert within the cell culture dish and attaching the insert to a surface of the dish (e.g. a bottom surface) in any suitable manner (in a nonlimiting example, adhering the insert), microwells can be provided more conveniently and consistently than with previous methods. Size of the well 64 (diameter, etc.), size/dimensions of the channels 66 (wider, narrower), distance between channels or wells, etc. can vary according to, for example, species, etc. The wells 64 can be used with known well of the well (WOW) methods for providing an in-vivo-like culture microenvironment for embryos. Further advantages are provided by channeled embodiments, as the oocytes/embryos can communicate with one another, for instance via embryotrophic factors (as a nonlimiting example), held together by the wells and channels in the insert 60.

Figure 7:
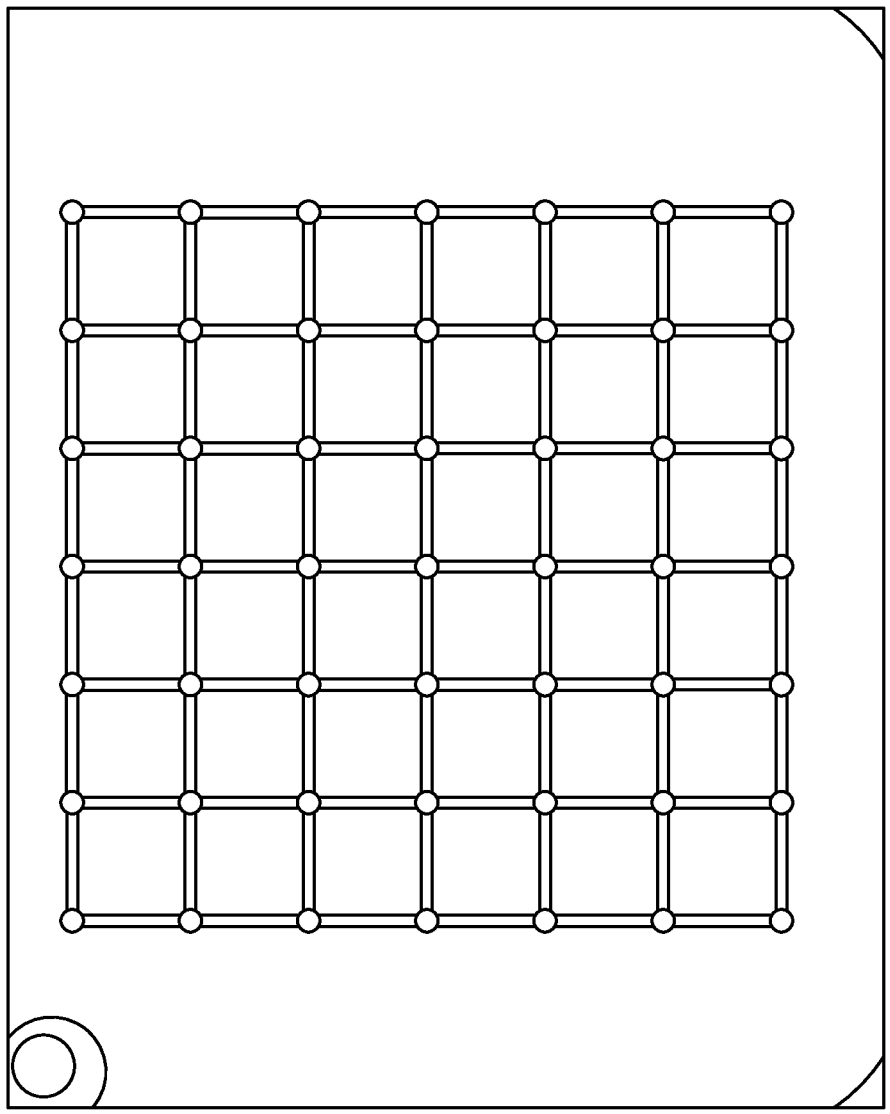
FIG. 7 shows a microfluidic well insert formed using PDMS.

FIG. 7 shows a particular example microfluidic well insert for embryo culture made of polydimethylsiloxane (PDMS). Those of ordinary skill in the art will appreciate example microfabrication techniques for forming wells and channels within PDMS. In this nonlimiting example, a 7×7 array of microfluidic wells is provided, where each microfluidic well has a diameter of 150 μM, a channel width of 100 μm, and a 1 mm distance along each row or column between adjacent wells. The dimensions of the wells (diameter, width, distance) can be changed depending on experimental purpose. However, soft lithography techniques allow each microfluidic well to have a precise, predefined configuration, providing uniformity.

Figure 8A:
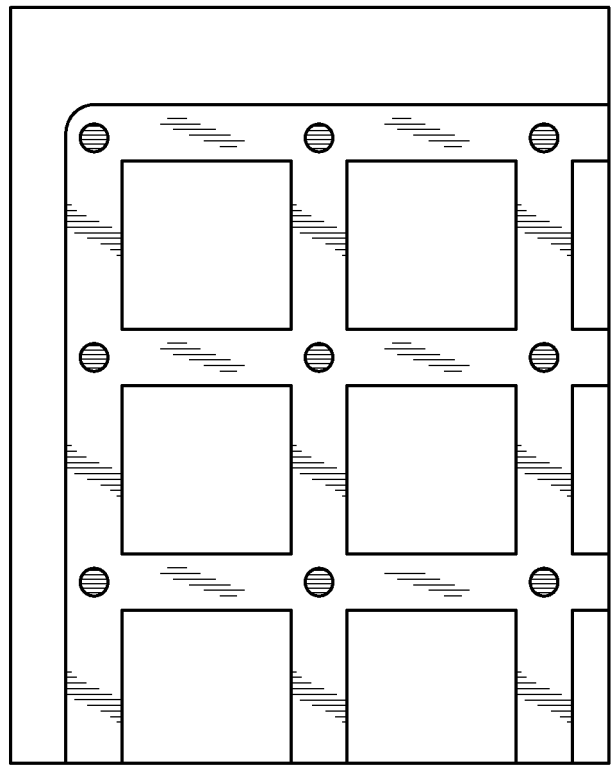
FIG. 8 shows an example method using the insert of FIG. 7.
Figure 8B:
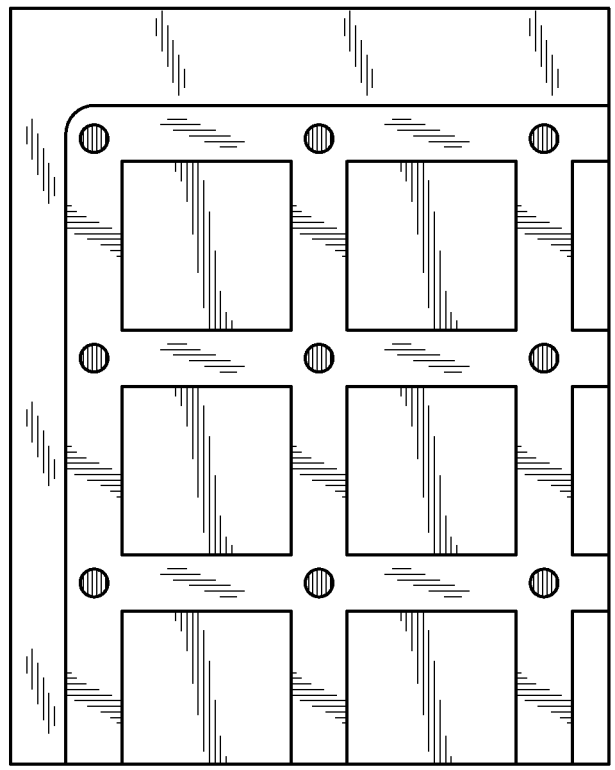

FIGS. 8A-8B show an example demonstration to verify marinating cell-cell communication, where FIG. 8A shows channel effect before a medium change, and FIG. 8B shows a channel effect after medium change. Particularly, the entire insert shown in FIG. 8A was covered with fluorescein isothiocyanate (FITC) solution. The FITC solution was changed with a blank medium of deionized (DI) water according to the standard medium change protocol, as shown in FIG. 8B. The FITC solution remained inside the channel undisrupted.

Figure 9:
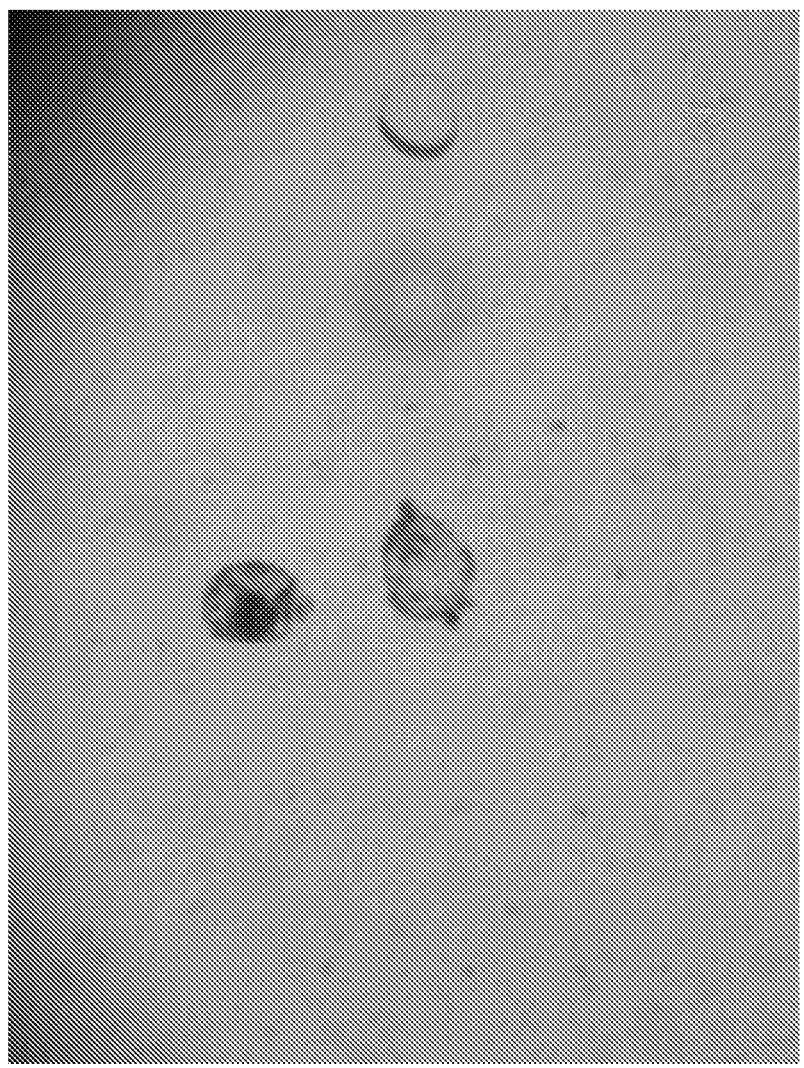
FIG. 9 shows blastocysts during an example operation using a channel-less insert, according to another embodiment of the present invention.

While FIGS. 7 and 8A-8B show a channeled embodiment, FIG. 9 shows a portion of an example channel-less embodiment. Within the microwells, successful development of bovine blastocysts was provided using example embryo/oocyte culturing methods and devices according to the present invention. In this example development, the blastocysts moved out of the wells as they grew in size, showing that methods using the WOW system can be used with example inserts according to the present invention.

Figure 10:
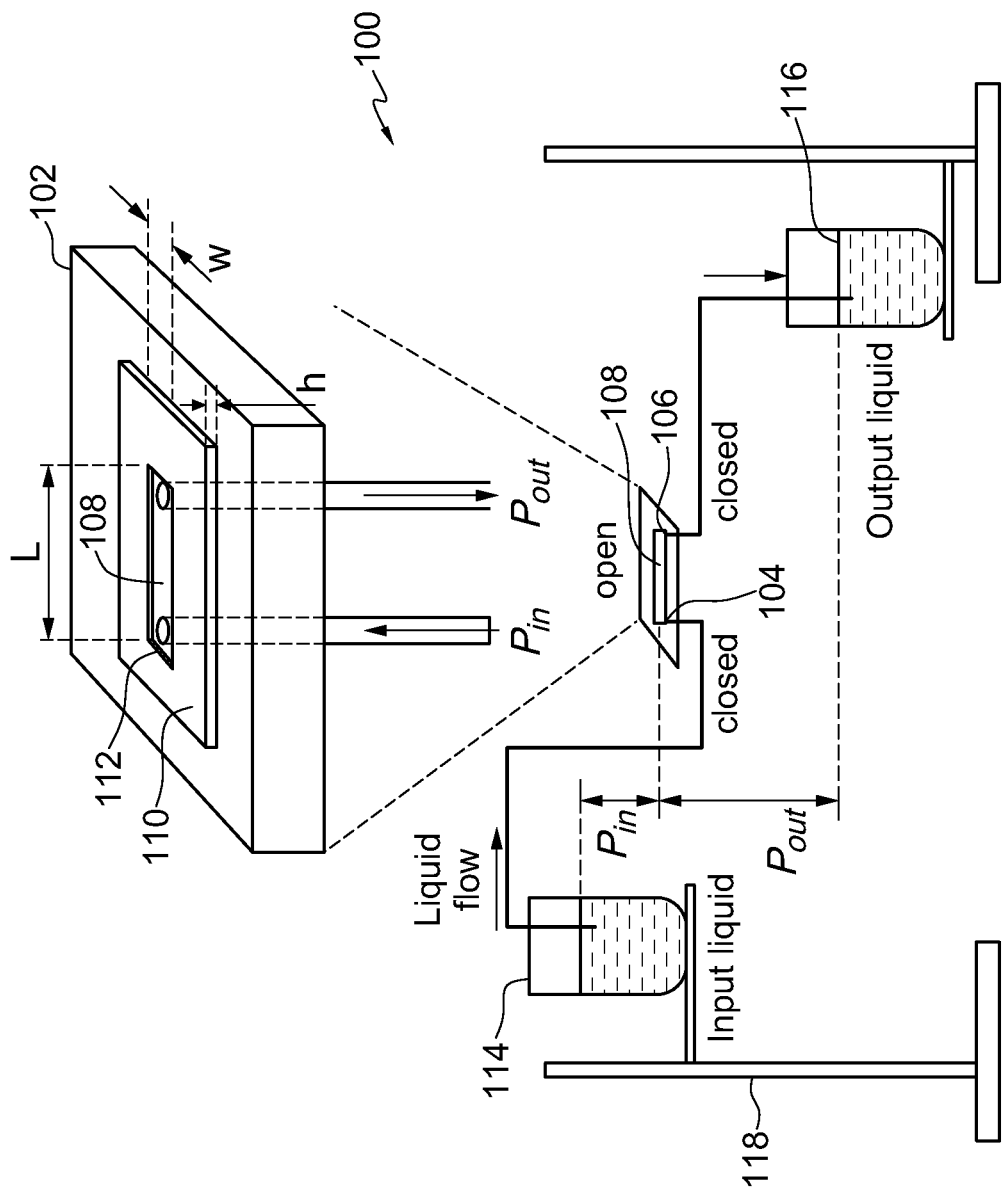
FIG. 10 shows a conventional closed-open-closed (COC) system.

Open-Closed-Open-Closed-Open (OCOCO) Microchannel System for Efficient Cell Culture and Convenient Sample Access Microchannel systems provide a good micro-environment for cell/embryo/oocyte culture and chemical analysis. However, it is inconvenient to load samples into or access samples from the microchannels. It has been previously suggested (e.g., Wijngaart et al., Behavior and design considerations for continuous flow closed-open-closed liquid microchannels, Lab on a Chip, 2005, 5(6): p. 682-686) to use a so-called closed-open-closed (COC) system for convenient sample access. An example of a COC system 100 and measurement setup is shown in FIG. 10. The COC system 100 includes a glass substrate 102 including a closed inlet port 104 and a closed outlet port 106 formed therein. An open microchannel 108 is formed using a PDMS substrate 110 that is disposed over the glass substrate 102. The PDMS substrate 110 includes an opening 112 surrounding both the inlet port 104 and outlet port 106 to define the microchannel.

For controlling fluid flow, the inlet port 104 is coupled to an input liquid 114, and the outlet port 106 is coupled to an output liquid 116, with the input liquid being disposed at a point higher than the microchannel 108 and the outlet liquid being disposed at a point lower than the microchannel. A suitable housing 118 can be provided to arrange the inlet liquid, microchannel, and outlet liquid.

Controlling a microchannel system such as the COC microchannel system 100 in FIG. 10 can be difficult. For example, certain systems do not allow cells to spread evenly within a microchannel (e.g., at a bottom of a microchannel) due to interaction between the particular cells used and the specific physical configuration of the microchannel between the inlet and the outlet. Thus, the results of such microchannels for particular cells during cell culturing (for instance) will vary according to the particular physical architecture of the microchannels, and vice versa. This means, among other things, that certain microchannels may not be optimal or even suitable for some cells, and vice versa. This deficiency is sometimes addressed in the art via external methods, but these methods may not always be successful.

Also, controlling a COC system such as the system 100 shown in FIG. 10 is not easy because the system typically relies on external pumping schemes such as hydrostatic pressure and syringe pumping, which need to be controlled carefully so that the liquid inside the channel does not overflow through the open microchannel. Further, the connecting tubes spend extra medium or reagent.

Figure 11:
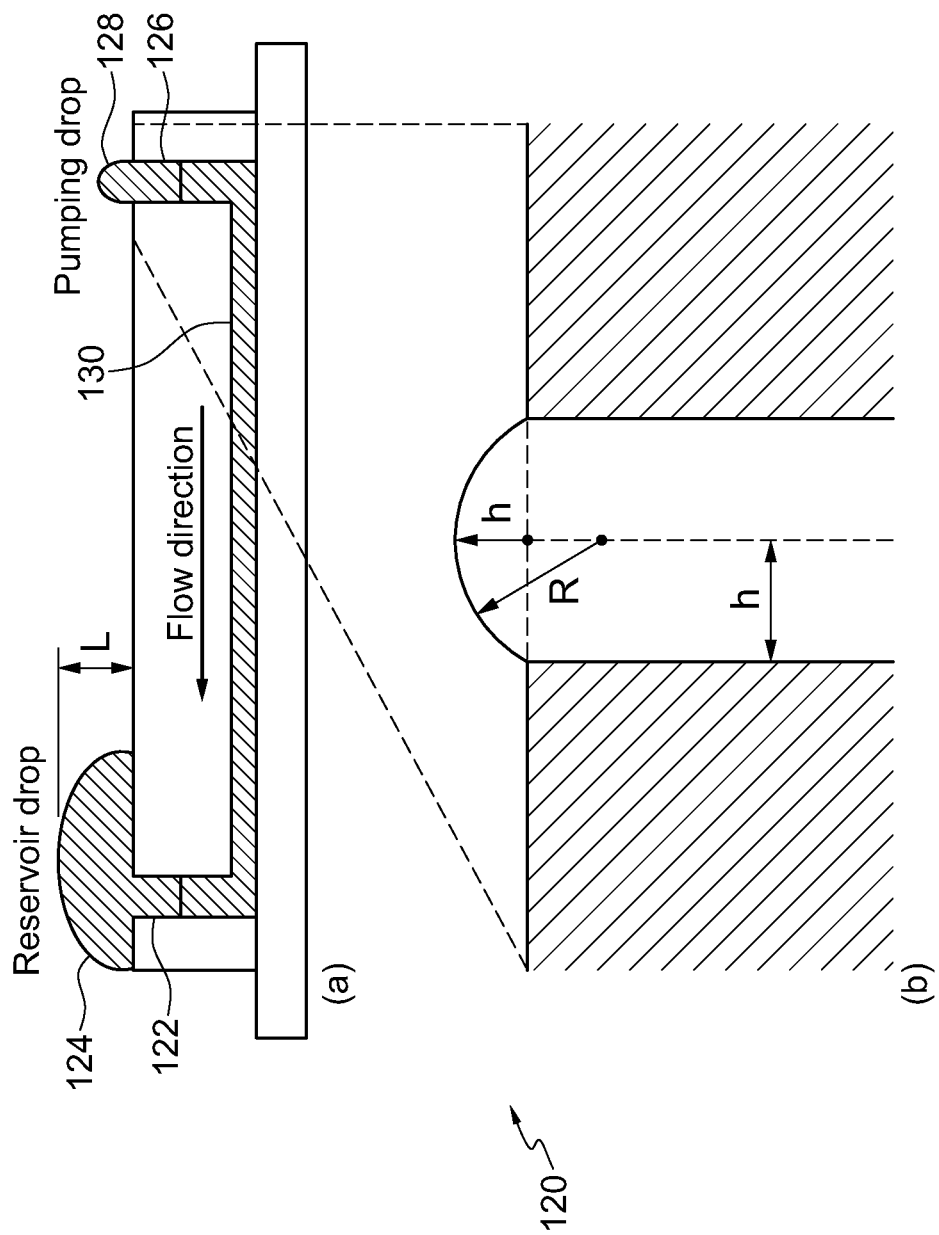
FIG. 11 shows a conventional open-closed-open (OCO) system.

Another type of microfluidic system uses a so-called open-closed-open (OCO) system for facilitating passive pumping. FIG. 11 shows an example OCO system 120. An open reservoir port 122 having a large drop 124 is coupled to a pumping port 126 having a smaller drop 128 via a closed microchannel 130. The larger drop 124 of the reservoir port 122 and the smaller drop 128 of the pumping port 126 are required for fluid flow. As shown in the enlarged portion of the pumping port 126, a drop of volume V forms a spherical cap of radius R on a port of radius r. The cap will rise above the surface of the device a distance h. If the drop volume is less than that for a hemisphere of radius r, then the drop radius R will be larger than h (e.g. see Walker et al., A passive pumping method for microfluidic devices, Lab On a Chip. 2002, 2(3): p. 131-134).

However, while the OCO passive pumping system 120 is a good way of pumping, it is difficult to access samples inside the microchannel 130. Samples can only be collected from the outlet of the microchannel by introducing new medium or reagent at the inlet port. Generally, this process requires dilution, and thus lowers the sample concentration of interest. Further, loading of cells and particles is inconvenient due to the nature of passive pumping. Loading of hydrogels for 3D culture or other research purposes, for example, is inconvenient due to the viscosity of hydrogels. High-throughput OCO methods, such as that disclosed by Meyvantsson et al., High Throughput Microfluidics, In Annual Fall Meeting of Biomedical Engineering Society, 2006, Chicago, Ill., USA, have been provided by expanding the OCO passive pumping. However, the above-mentioned problems with passive pumping have not been addressed. Thus, certain types of cells remain difficult or impossible to grow using some conventional systems.

The present inventors have discovered that it is desirable to open up a microchannel so that cells, media, etc. can be accessed within the microchannel. This allows, among other things, cells to be more evenly loaded in channels. For example, cell cultures may grow in the port area. By opening this up, the medium can be kept in the channel. The channel may not need to be closed. For these and other reasons, it can be useful to provide an improved way to get cells, media, etc. into and out of a microchannel.

Embodiments of the present invention provide, among other things, a microchannel system having an inlet and outlet opening, and an additional opening disposed therebetween, referred to herein as an open-closed-open-closed-open (OCOCO) system. Such a system can accommodate a micro-environment using passive pumping to change a medium or a reagent. In this way, example systems do not require any connecting channels or tubing and thus extra medium or reagent is not wasted. Also, embodiments of the present invention provide a convenient way to collect samples from the open window without any dilution effect. The complexity of control in the COC system is avoided. The open window provides a convenient way to load cells, particles, and hydrogels. Example systems can easily be expanded to a high-throughput system.

An example OCOCO system 130 is shown in FIGS. 12A-12B. Within a substrate 132, an inlet 134 (shown with a small drop) and an outlet 136 (shown with a large drop) are provided at opposing ends, connected by at least one microchannel 140. Disposed between the inlet 132 and the outlet 134, and along the microchannel 140, is an open window provided by an opening 142 in the substrate 132 that allows access, for example, to a cell within the channel. An extra space 144 may be provided within the microchannel 140 below the opening 142 and between other portions 146 of the microchannel, for providing (for instance) a well, such as but not limited to a well for a three-dimensional hydrogel culture. Fabrication techniques for the example OCOCO system will be apparent to those of ordinary skill in the art having reference to the disclosure herein. The well provided in the space 144 can be used, in nonlimiting example methods, for growing cells on, e.g., hydrogel for flowing over, then retrieval. The OCOCO system 130 can be fabricated using methods and materials such as those described herein with respect to other embodiments disclosed herein. In a nonlimiting example embodiment, the OCOCO system can be made by bonding two layers of PDMS to provide one layer for the microchannels 140, ports 134, 136, openings 142, and another for the well 144. The two layers can then be bonded (e.g., above the well space 144 and below the formed microchannel 140) to provide the components. Examples of items to access the opening 142 include but are not limited to pipettes and needles, and the opening may be used, as nonlimiting examples, for harvesting cells for DNA analysis, harvest cells for biochemical assays, histology, etc.

In operation, liquid flows from the inlet 134 to the outlet 136 by passive pumping. For example, the inlet 134 may be loaded with fluid, providing a bigger droplet at the outlet 136 and thus lower pressure due to the resulting lower surface to volume ratio. Adding more fluid passively pumps fluid when introduced, first by capillary action, then due to the lower pressure on the other side. In other words, the high surface to volume ratio on the inlet 134 relative to the lower surface to volume ratio on the larger drop at the outlet 136 causes the introduced fluid to move from high to low, through the microchannel 140, inducing flow. The liquid level of the open window 142 is maintained constantly. The open window 142 allows the cells to be evenly loaded in the channel 140. Without the open window 142, by contrast, a substantial number of the cells would stay at the port area, which would bias the cell culture. By loading the cells directly through the open window 142, they can be distributed evenly. The example OCOCO channel 130 can be used similarly to other microchannels, but further provides a way to access the microchannel.

Figure 13:
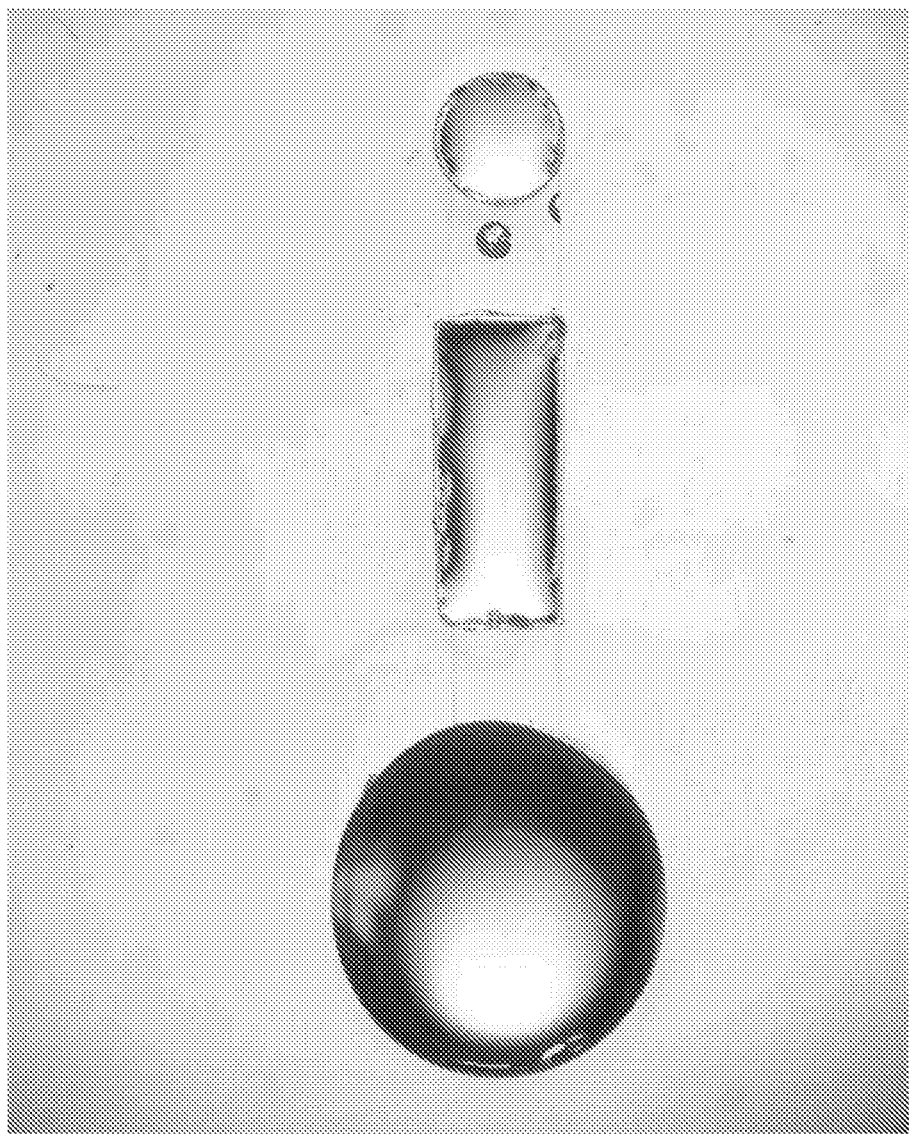
FIG. 13 shows an example OCOCO formed by forming openings into a polydimethylsiloxane (PDMS) substrate.

In a nonlimiting example application, during osteogenic differentiation, cells overlap to make nodules, which require more space. Embodiments of the present invention having an open window 142 will provide a more suitable environment for osteogenic differentiation while maintaining passive pumping. Further, for a three-dimensional (3D) culture using hydrogels, it is even more difficult to load cells and gels inside a microchannel without an open window due to the viscosity of hydrogels. The open window can also provide better air diffusion when compared to the microchannels without the open window. FIG. 13 shows an example OCOCO system formed in a substrate. Operation of the example system shown in FIG. 13 allowed the passive pumping to work well while maintaining the level of the liquid in the open window.

Figure 14:
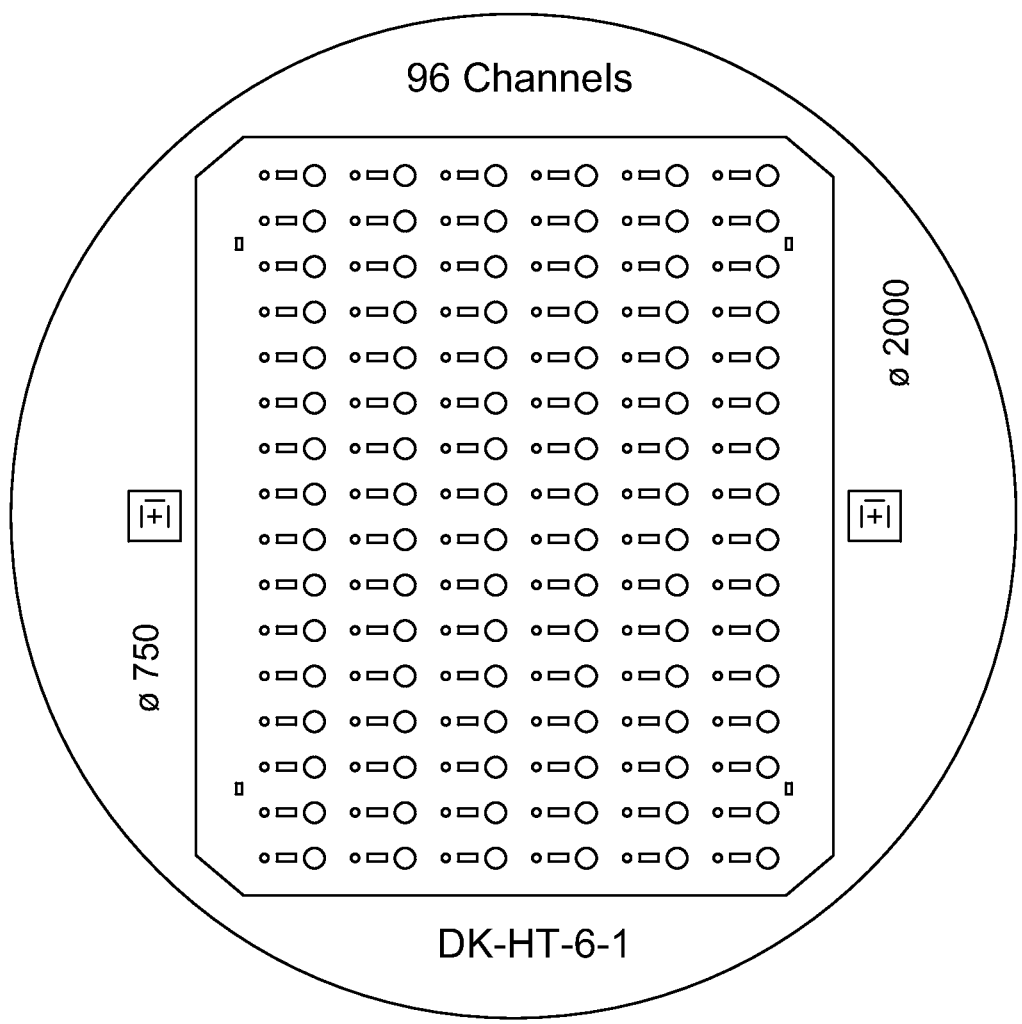
FIG. 14 shows an example photomask for using during an example fabrication method for a high-throughput OCOCO system.

As with other embodiments of the present invention, an example OCOCO system can be expanded to provide a high-throughput system. As shown in FIG. 14, a photomask can be used in a method to make an array of micro-OCOCO channels in a substrate, each having an inlet, outlet, and open window disposed therebetween. A fluid handling robot can be incorporated in example embodiments to aspirate and dispense medium or reagent. The nonlimiting example array provided (in part) by the photomask in FIG. 14 is a two-dimensional array of 96 (6×16) micro-OCOCO channels. Other example arrays number 192, 384, or more (or fewer) micro-OCOCO channels on a substrate. A nonlimiting example substrate is a micro-titer plate, such as a standard micro-titer plate.

Top-Off System for Microfluidics and Automated Pipetting Systems Using a Surface Tension Based Valve Though cell culturing can be a time-consuming, labor intensive, and/or error-prone process, efficiencies can be introduced with high-throughput systems. Examples of such high-throughput systems are shown and described herein, with several applications. Certain high-throughput systems, though, are limited by current automated pipetting systems. For example, media changes can be particularly acute, requiring extensive setup and trained operators. Even so, operator error typically is not eliminated. Due to these and other concerns, the time savings provided by current automated pipetting systems may be only moderate.

In a microfluidic system, to aspirate and dispense a predetermined amount of a sample liquid, it is important to prevent the outside of a pipette tip from wetting by the sample liquid. If this is not done, the sample will contaminate or wet the outside of the tip, which will cause a dispensing error. This problem is especially concerning for automatic fluid handling, where a dispensing error can bias the result or cause malfunction of a high-throughput screening (HTS) system.

If the tip only touches the surface of the liquid, the problem can be minimized. However, touching the surface of the liquid is difficult to achieve, especially for automatic fluid handling robots. While a very expensive pipettor can sense the level of a fluid, such a sensing mechanism is hardly applicable for a multi-channel pipettor.

Thus, additional embodiments of the present invention provide, among other things, an automatic top-off system using a surface tension based valve, which in an example embodiment requires neither any moving parts nor electronic control devices. Further, an example top-off system is inexpensive and convenient to miniaturize for microfluidic and/or high-throughput systems.

A liquid handling system is provided according to embodiments of the present invention to automatically fill wells, e.g., culture wells, to desired levels without operator handling. In an example system, fluids are stored in a separate reservoir, and tubing is specifically allocated to each well. More particularly, a siphon system passes media from a fluid reservoir to individual wells based on surface tension of the receiving well. Liquid is passively added while a seal, such as a valve cap, remains open. After the seal is closed and initial flow is induced, the liquid media is maintained in an aspiration well at a constant level, without manual manipulation. Nonlimiting example applications include high-throughput cell culture and high-throughput in vitro drug screening.

Figure 15:
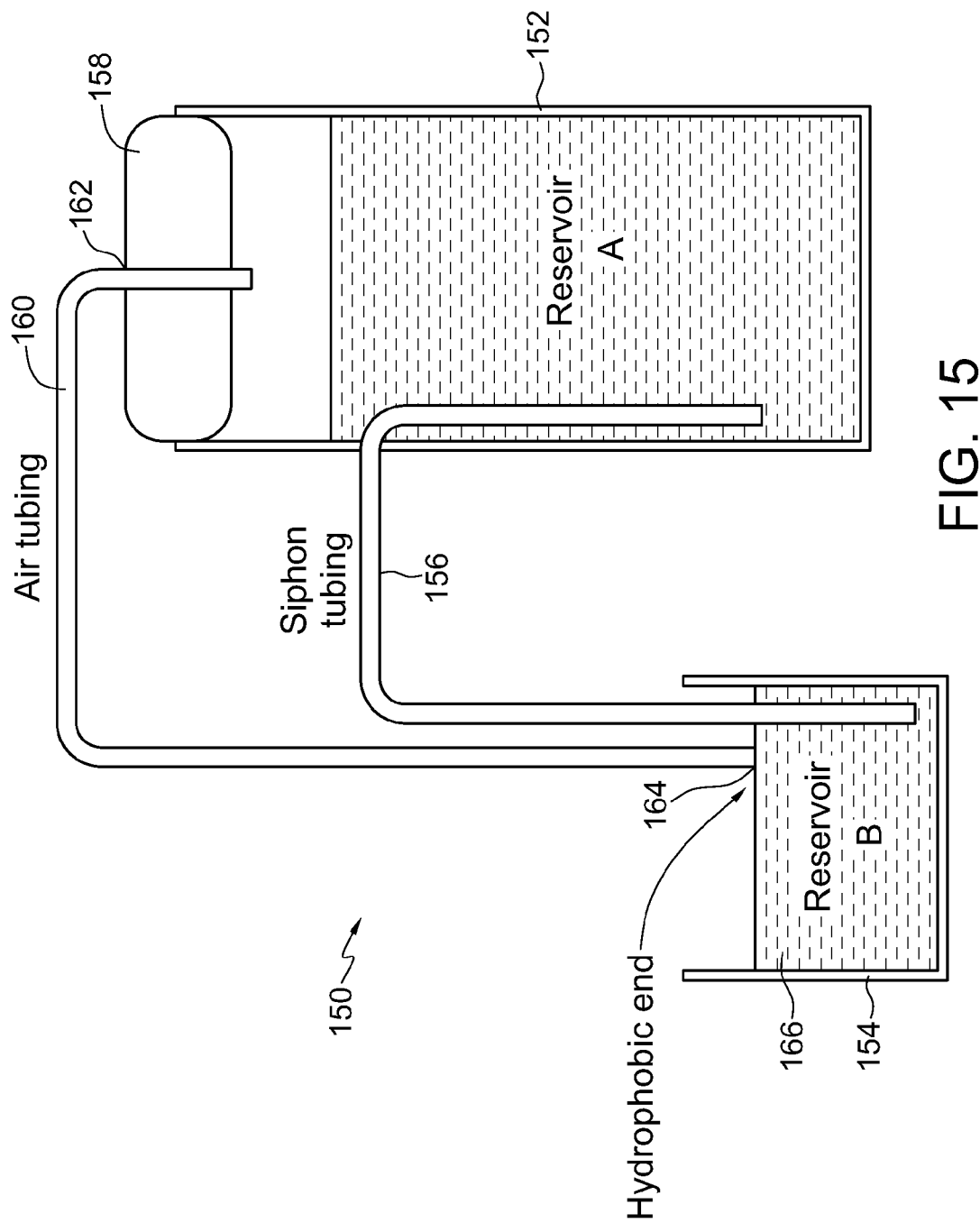
FIG. 15 shows an example fluidic system for dispensing a predetermined amount of a liquid, according to another embodiment of the present invention.

FIG. 15 shows an example automatic top-off system 150 illustrating principles of an embodiment of the present invention. In the example top-off system 150, two reservoirs (e.g., Reservoir A 152 and Reservoir B 154) are provided. The Reservoirs A and B 152, 154 are connected by siphon tubing 156, such as any suitable fluid tubing. Reservoir A 152 serves as a fluid reservoir or main reservoir, and Reservoir B 154 serves as a receiving well, culture well, or aspiration well. Reservoir A 152 is closed using a suitable valve seal, such as but not limited to a cap 158 having an air tubing 160 passing through an opening 162 of the cap. The air tubing 160 leads back to Reservoir B 154. According to an embodiment of the present invention, an end 164 of the air tubing 160 leading to the aspiration well (Reservoir B) 154 is treated as hydrophobic. In a nonlimiting example, the hydrophobic end 164 is treated using a self-assembled monolayer (SAM).

Being provided with the hydrophobic end 164 leading to Reservoir B 154, the example air tubing 160 serves as an automatic liquid level valve. For example, usually the air tubing 160 can be easily closed due to the capillary motion of the liquid 166 when it touches the surface of the liquid, and once this happens the siphon will not work. However, the hydrophobic end 164 of the air tubing 160 prevents the capillary motion by surface tension, and thus provides an automatic top-off function.

Thus, in an example operation, initially, the liquid from Reservoir A 152 goes into Reservoir B 154 through the siphon tubing 156 when slight negative pressure is applied into Reservoir B, such as but not limited to using vacuum tubing. Liquid 166 is passively added as the surface tension drops so long as the valve cap 158 remains open. Once the liquid level 166 of Reservoir B 154 reaches the hydrophobic end 164 of the air tubing 160, liquid filling stops, because the hydrostatic pressure of Reservoir A 152 and the surface tension of the hydrophobic end of the air tubing are balanced. The liquid media 166 is thus maintained in Reservoir B at a constant level without manual manipulation.

Figure 16:
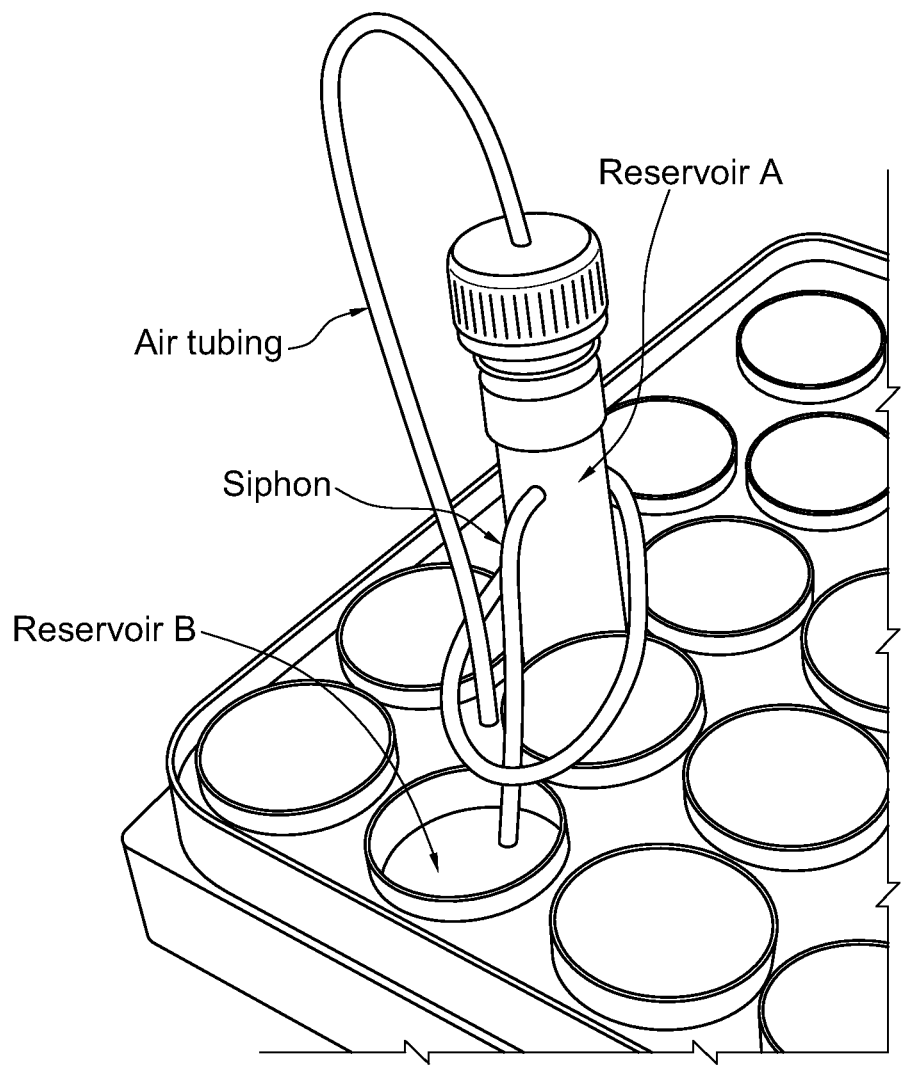
FIG. 16 shows an example dispensing system for dispensing liquid from a vial into one or more wells.

FIG. 16 shows an example simple reservoir system for controlling a liquid level. A well in a multi-well plate, for instance a 24-well plate having a plurality of culture wells, provides an aspiration well (Reservoir B). A vial coupled to the plate, for instance a 2 mL vial, provides a separate, main reservoir (Reservoir A). Siphon tubing leads from the liquid in the vial through a portion of the vial body, and to the aspiration well. A cap is fitted over the vial, the cap having an opening for accommodating plastic air tubing but otherwise sealing the vial. An end of the air tubing leading to Reservoir B is treated to be hydrophobic. The tubing can be specifically allocated to each well. The hydrophobic end of the air tubing is able to control the liquid level. Depending on the size of the system and hydrostatic pressure, different sizes or number of hydrophobic tubing may be used. According to an example embodiment, a consistent fluid height can be provided in the aspiration well. In this way, a fluid handling robot or other device or user can obtain fluid from the aspiration well in a consistent manner without having to adjust to varying fluid heights. This in turn allows easier automatic fluid handling, e.g., pipetting, while overcoming concerns of some conventional methods. It will be appreciated that even though various embodiments of the present invention have been described separately, the present invention is intended to include any combination of the embodiments described herein. In a nonlimiting example, multiple example embodiments can be combined and coupled via suitable fluid coupling to provide microfluidic systems for cell-based microfluidic manipulation, formed on a single substrate or on multiple substrates. A nonlimiting example system is a high-throughput IVF system. The automatic top-off system can also be used in combination with any of the other methods.

While various embodiments of the present invention have been shown and described, it should be understood that other modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. A microfluidic system for assaying a plurality of cells, the microfluidic system comprising:
    a substrate defining a plane; and
    a plurality of microfluidic channels arranged in the substrate, each of said plurality of microfluidic channels comprising:
        a source channel at an end of said microfluidic channel and a sink channel at an opposing end, said source channel having an inlet and an outlet and fluidly connecting said inlet and outlet of said source channel along the plane, said sink channel having an inlet and an outlet and fluidly connecting said inlet and outlet of said sink channel along the plane;
        a cell chamber disposed within said microfluidic channel between said source channel and said sink channel;
        a cell inlet and a fluid outlet in fluid communication with said cell chamber, said cell inlet being fluidly connected to the cell chamber along the plane by a first channel, and said fluid outlet being fluidly connected to the cell chamber along the plane by a second channel;
        each of said source channel, said sink channel, and said first and second channels being narrower along the plane than said cell chamber;
    further comprising:
    a medium disposed in said source channel, said cell chamber, and said sink channel;
    at least one cell provided within the medium of said cell chamber;
    an attractant provided within the medium of only said source channel, wherein the medium disposed in said sink channel is a blank medium;
    wherein fluid flow is restricted and diffusion is permitted between said cell chamber and said sink channel; and
    wherein fluid flow is restricted and diffusion is permitted between said cell chamber and said source channel;
    wherein a concentration gradient of the attractant is formed within said cell chamber between said source channel and said sink channel.

2. The microfluidic system of claim 1, wherein the substrate comprises PDMS, and wherein said plurality of microfluidic channels are formed within the substrate by microfabrication.

3. The microfluidic system of claim 1, wherein said substrate is coupled with a base;
    wherein at least one of the plurality of microfluidic channels is at least partially defined by a surface of the base.

4. The microfluidic system of claim 1, wherein said source channel and said sink channel for each of the plurality of microfluidic channels are disposed along said substrate to align with a fluid handling robot.

5. The microfluidic system of claim 1
    wherein a fluidic resistance is disposed between said cell chamber and said sink channel; and
    wherein a narrow portion of the microfluidic channel is disposed between said source channel and said cell chamber.

6. The microfluidic system of claim 5, wherein the narrow portion of the microfluidic channel comprises a wedge.

7. The microfluidic system of claim 1
    wherein a fluidic resistance is disposed between said cell chamber and said source channel; and
    wherein a narrow portion of the microfluidic channel is disposed between said sink channel and said cell chamber.

8. The microfluidic system of claim 1, wherein said cell chamber is either pyramidal or square shape.

9. The microfluidic system of claim 1
    wherein a fluidic resistance is disposed between said sink channel and said cell chamber; and
    wherein said fluidic resistance comprises at least one protrusion formed in said microfluidic channel.

10. The microfluidic system of claim 1, wherein each of the inlet and the outlet of said source channel, the inlet and outlet of said sink channel, said cell inlet, and said fluid outlet for each of the plurality of microfluidic channels are aligned in arrays on said substrate.

11. The microfluidic system of claim 10, wherein the arrays are one-dimensional.

12. The microfluidic system of claim 10, wherein the arrays are two-dimensional.

13. The microfluidic system of claim 12, wherein the plurality of microfluidic channels comprises at least 96 microfluidic channels.

14. The microfluidic system of claim 1, wherein said cell chamber is hourglass shaped.

15. The microfluidic system of claim 1, wherein a fluidic resistance is disposed between said cell chamber and said sink channel to restrict fluid flow and permit diffusion;
wherein said fluidic resistance comprises an array of narrow channels.

16. The microfluidic system of claim 1, wherein said cell chambers of at least two of the plurality of microfluidic channels have respectively different shapes.

17. The microfluidic system of claim 1;
wherein each of said inlet and outlet of said source channel are wider than said source channel along the plane;
wherein each of said inlet and outlet of said sink channel are wider than said sink channel along the plane; and
wherein each of the cell inlet and the fluid outlet are wider than said first channel and said second channel along the plane.

18. A method for assaying using a microfluidic system for assaying a plurality of cells, the microfluidic system comprising a substrate and a plurality of microfluidic channels arranged in the substrate; each of said plurality of microfluidic channels comprising a source channel at an end of said microfluidic channel and a sink channel at an opposing end, said source channel having an inlet and an outlet, a cell chamber disposed within said microfluidic channel between said source channel and said sink channel, and a cell inlet in fluid communication with said cell chamber; the microfluidic system further comprising a medium disposed in said source channel, said cell chamber, and said sink channel, at least one cell provided within the medium of said cell chamber, and an attractant provided within the medium of only said source channel, wherein the medium disposed in said sink channel is a blank medium, wherein fluid flow is restricted and diffusion is permitted between said cell chamber and said sink channel, wherein fluid flow is restricted and diffusion is permitted between said cell chamber and said source channel, and wherein a concentration gradient of the attractant is formed within said cell chamber between said source channel and said sink channel, the method comprising:
loading the medium into said cell chamber, said source channel, and said sink channel;
loading the at least one cell into said cell chamber via said cell inlet;
introducing an attractant into said source channel, but not said sink channel;
wherein the concentration gradient in the medium is developed within said cell chamber due to diffusion;
wherein said sink channel provides a zero boundary condition for forming the concentration gradient.

19. The method of claim 18, wherein the concentration gradient has a generally radial shape.

20. The method of claim 18, further comprising:
assessing movement of the at least one cell along the concentration gradient.

21. The method of claim 18, wherein the attractant comprises a chemoattractant.

22. The method of claim 18, wherein fluidic resistance separates said cell chamber fluidically from said sink channel but permits passage of molecules by diffusion.

23. The method of claim 18, wherein the concentration gradient is measurable in cylindrical coordinates.

24. The method of claim 18, wherein the concentration gradient is two-dimensional.

25. A microfluidic system for assaying a plurality of cells, the microfluidic system comprising:
a PDMS substrate;
a base coupled to said substrate; and
a plurality of microfluidic channels arranged in the substrate and formed by microfabrication, each of said plurality of microfluidic channels comprising:
a source channel at an end of said microfluidic channel and a sink channel at an opposing end, said source channel and said sink channel having an inlet and an outlet;
a cell chamber disposed within said microfluidic channel between said source channel and said sink channel;
a cell inlet in fluid communication with said cell chamber; and
wherein fluid flow is restricted and diffusion is permitted between said cell chamber and said sink channel; and
wherein fluid flow is restricted and diffusion is permitted between said cell chamber and said source channel;
wherein the cell chamber narrows in width along a direction from one of said source channel and said sink channel to the other of said source channel and said sink channel to a narrow portion of the microfluidic channel that is disposed between said cell chamber and the other of said source channel and said sink channel, wherein the narrow portion provides fluidic resistance and permits diffusion;
wherein the inlet and the outlet of said source channel, the inlet and outlet of said sink channel, and said cell inlet for each of the plurality of microfluidic channels are aligned in two-dimensional arrays on said substrate;
wherein said cell chamber is configured to provide a radial concentration gradient within the cell chamber.

* * * * *